US007829341B2

(12) United States Patent
Gamsey et al.

(10) Patent No.: US 7,829,341 B2
(45) Date of Patent: Nov. 9, 2010

(54) POLYVIOLOGEN BORONIC ACID QUENCHERS FOR USE IN ANALYTE SENSORS

(75) Inventors: Soya Gamsey, Huntington Beach, CA (US); Ritchie A. Wessling, Watsonville, CA (US)

(73) Assignee: Glumetrics, Inc., Irvine, CA (US)

( * ) Notice: Subject to any disclaimer, the term of this patent is extended or adjusted under 35 U.S.C. 154(b) by 293 days.

(21) Appl. No.: 12/172,059

(22) Filed: Jul. 11, 2008

(65) Prior Publication Data

US 2009/0081803 A1      Mar. 26, 2009

Related U.S. Application Data

(60) Provisional application No. 60/949,145, filed on Jul. 11, 2007.

(51) Int. Cl.
| | |
|---|---|
| *G01N 33/52* | (2006.01) |
| *G01N 33/66* | (2006.01) |
| *G01N 21/64* | (2006.01) |
| *C07D 213/22* | (2006.01) |
| *C07F 5/02* | (2006.01) |

(52) U.S. Cl. .................... 436/95; 422/82.07; 422/82.08; 436/94; 436/166; 436/172; 546/13; 546/257; 546/258

(58) Field of Classification Search ................ 422/68.1, 422/82.05–82.08; 436/94–95, 166, 172; 546/13, 257–258; 564/79, 85
See application file for complete search history.

(56) References Cited

FOREIGN PATENT DOCUMENTS

| WO | WO 2007/067743 A2 | 6/2007 |
|---|---|---|
| WO | WO 2008/098087 A2 | 8/2008 |
| WO | WO 2008/137604 A1 | 11/2008 |

OTHER PUBLICATIONS

Sato, H. et al, Journal of Applied Polymer Science 1979, 24, 2075-2085.*
Atherton, S. J. et al, Journal of the American Chemical Society 1986, 108, 3380-3385.*
Tsukahara, K. et al, Bulletin of the Chemical Society of Japan 1999, 72, 139-149.*
Park, Y. S. et al, Langmuir 2000, 16, 4470-4477.*
Lee, S. K. et al, Journal of the Chemical Society, Perkin Transactions 2 2001, 1983-1988.*
Roman, E. et al, Tetrahedron 2002, 58, 699-709.*
DiCesare, N. et al, Langmuir 2002, 18, 7785-7787.*
Takashima, H. et al, Journal of Biological Inorganic Chemistry 2003, 8, 499-506.*
Kuwabara, T. et al, Photochemistry and Photobiology 2003, 77, 572-575.*
Cao, H. et al, Journal of Fluorescence 2004, 14, 569-584.*
Cordes, D. B. et al, Langmuir 2005, 21, 6540-6547.*
Gamsey, S. et al, Langmuir 2005, 22, 9067-9074.*
Hvastkovs, E. G. et al, . et al, Langmuir 2005, 22, 10821-10829.*
Sharrett, Z. et al, Tetrahedron Letters 2008, 49, 300-304.*
Gamsey, S. et al. 2007 "Boronic acid based bipyridinium salts as tunable receptors for monosaccharides and α-hydroxycarboxylates" *J Am Chem Soc* 129:1278-1286.
Hirata O. et al. 2002 "Allosteric saccharide sensing by a phenylboronic-acids-appended 5,15-bis(triarylethynyl)porphyrin" *J Supramolecular Chemistry* 2:133-142.
Suri, J. et al. 2003 "Continuous glucose sensing with a fluorescent thin-film hydrogel" *Angew Chem Int Ed* 42:5857-5859.
Wang, D. et al. 2001 "Photoluminescence quenching of conjugated macromolecules by bipyridinium derivatives in aqueous media: charge dependence" *Langmuir* 17:1262-1266.

* cited by examiner

*Primary Examiner*—Arlen Soderquist
(74) *Attorney, Agent, or Firm*—Knobbe Martens Olson & Bear LLP

(57) ABSTRACT

The invention relates to a class of glucose-responsive, polyviologen boronic acid quenchers that may be used in combination with fluophores to achieve real-time measurement of glucose levels in vivo.

28 Claims, 2 Drawing Sheets

POLYVIOLOGEN BORONIC ACID QUENCHERS FOR USE IN ANALYTE SENSORS

RELATED APPLICATIONS

This application claims the benefit of U.S. Provisional Application No. 60/949,145 filed Jul. 11, 2007 which is hereby incorporated by reference in its entirety.

FIELD OF THE INVENTION

The invention relates generally to the detection of polyhydroxyl-substituted organic molecules and in particular to polyviologens functionalized with boronic acids as quenchers of fluorescent dyes.

DESCRIPTION OF THE RELATED ART

Fluorescent dyes and analyte-binding moieties that modulate fluorescence upon binding analyte are known and have been used in indicator systems for analyte detection. See e.g., U.S. Pat. Nos. 6,653,141, 6,627,177, 5,512,246, 5,137,833, 6,800,451, 6,794,195, 6,804,544, 6,002,954, 6,319,540, 6,766,183, 5,503,770, and 5,763,238; and co-pending U.S. patent application Ser. Nos. 10/456,895, 11/296,898, 11/671,880, 60/833,081, 60/888,477, and 60/888,475; each of which is incorporated herein in its entirety by reference thereto.

More particularly, investigators have used fluorescent techniques to measure polyhydroxyl compounds (e.g., glucose) concentrations in body fluids. For example, Russell, disclosed the use of a boronic acid functionalized dye that binds to glucose and generates a signal dependent on glucose concentration (U.S. Pat. No. 5,512,246). James et al. used the same principle but combined a fluorescent dye, an amine quenching functionality, and a boronic acid in a single complex moiety, the fluorescence emission from which varies with the extent of glucose binding (U.S. Pat. No. 5,503,770). Glucose sensors comprising a fluorescent dye and a quencher comprising a single viologen moiety appended with boronic acids have been synthesized and investigated (e.g., Gamsey, S. et al. 2006 *Langmuir* 22:9067-9074; Thoniyot, P. et al. 2006 *Diabetes Technol Ther* 8:279-287; Cordes, D. B. et al. 2005 *Langmuir* 21:6540-6547; Cordes, D. B. et al. 2005 *Org Biomol Chem* 3:1708-1713; and Cappuccio, E. E. et al. 2004 *J Fluoresc* 14:521-533).

SUMMARY OF THE INVENTION

Polyviologen compounds comprising two or more viologen moieties, wherein each viologen moiety includes at least two boronic acid functional groups and wherein the polyviologen compound comprises a coupling group are disclosed in accordance with the preferred embodiments of the present invention.

Preferred embodiments include polyviologen compounds derived from 3,3' dipyridyl intermediates comprising two or more viologen moieties, wherein each viologen moiety includes at least two boronic acid functional groups and wherein at least one of the rings of the 3,3'dipyridyl intermediate is substituted with a coupling group. In some embodiments, the coupling group is a carboxyl group.

A bis-viologen quencher B, having the generic structure shown below is disclosed in accordance with the preferred embodiments of the present invention.

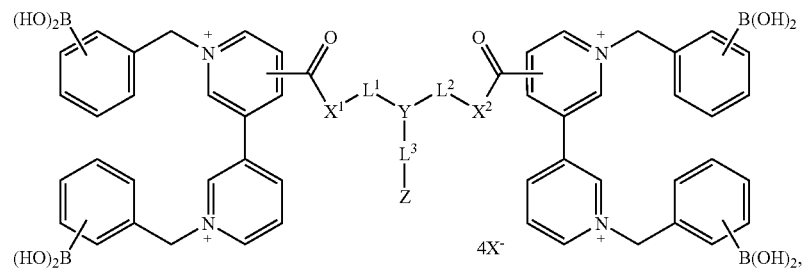

wherein

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

wherein R is H or CH$_3$;

Y is a trivalent connecting group selected from

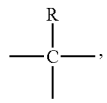

where R is H or a lower alkyl, and

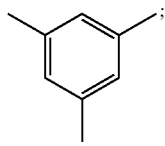

$X^-$ is a counterion;

$X^1$ and $X^2$ are —O— or —NH—; and $L^1$, $L^2$, and $L^3$ are selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH(C═O)—O—, urea —NH(C═O)NH—, thiourea —NH(C═S)—NH—, amide —(C═O)NH—, amine —NR— (where R is defined as alkyl having 1 to 6 carbon atoms) or combinations thereof.

A quencher "B" having the variations B-1, B-2, B-3 and B-4 shown below is disclosed in accordance with preferred embodiments of the present invention.

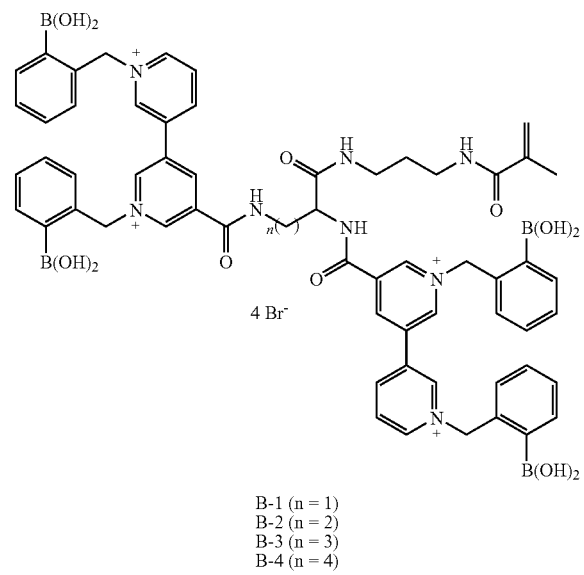

B-1 (n = 1)
B-2 (n = 2)
B-3 (n = 3)
B-4 (n = 4)

A method of making B-1, B-2, B-3 and B-4 is disclosed in accordance with another embodiment of the present invention, comprising the steps of:

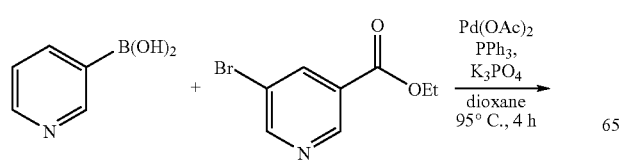

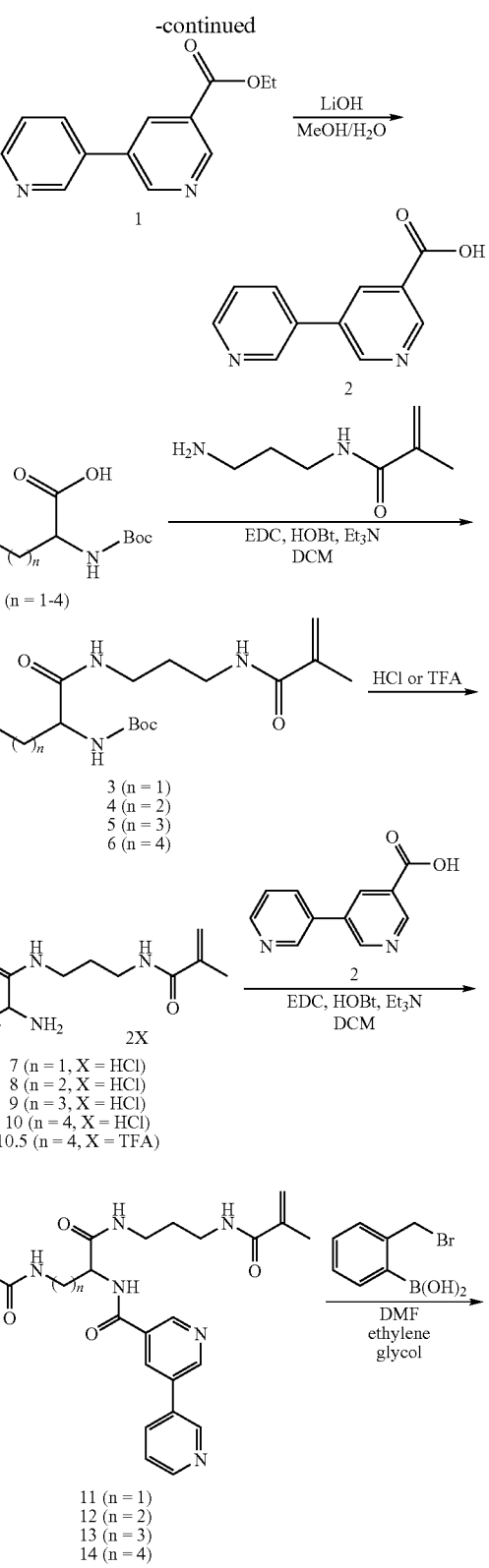

wherein compound 2 is a 3,3' dipyridyl intermediate.

In another embodiment, an alternate method of making B-4 comprises the steps of:
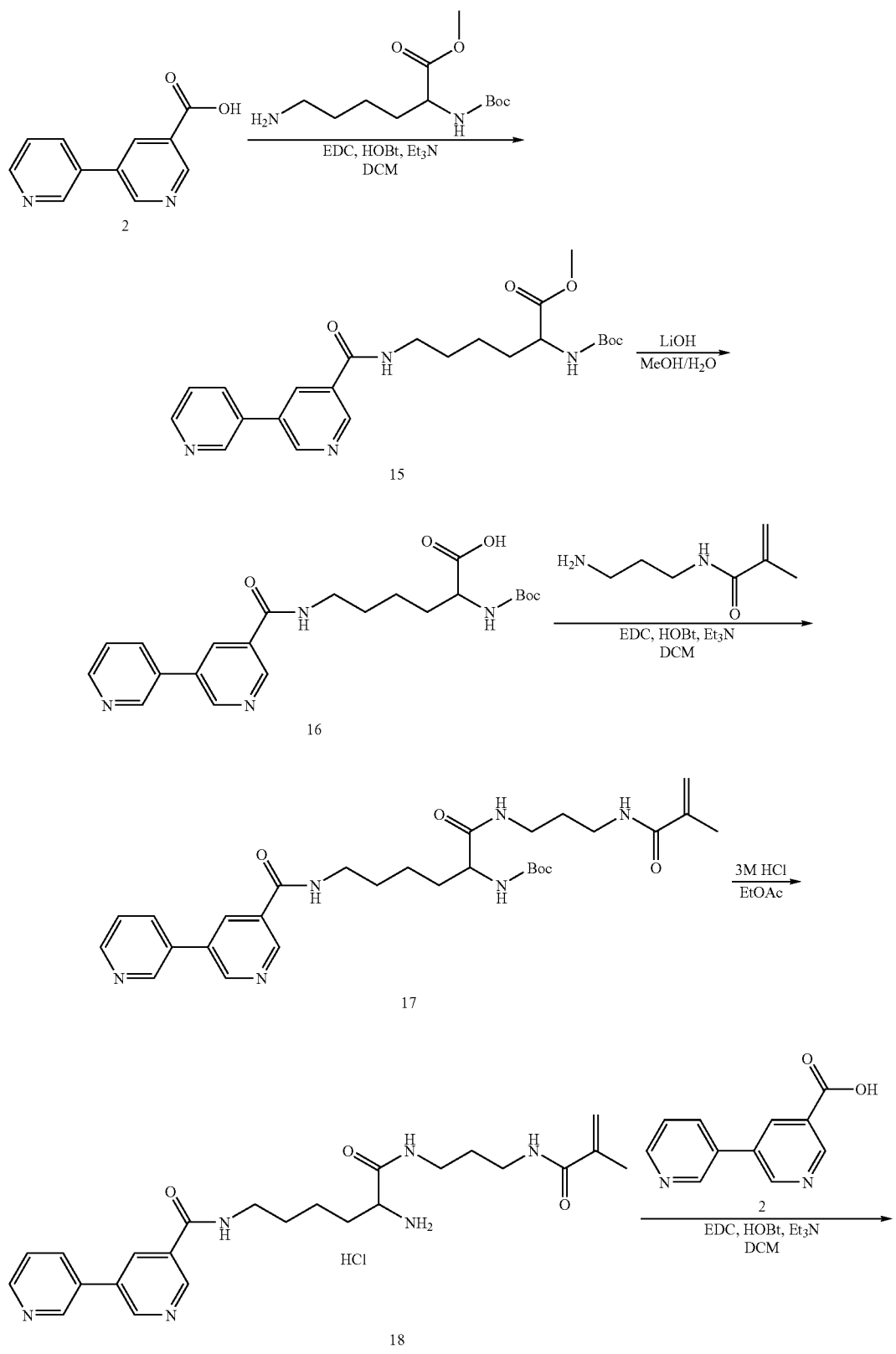

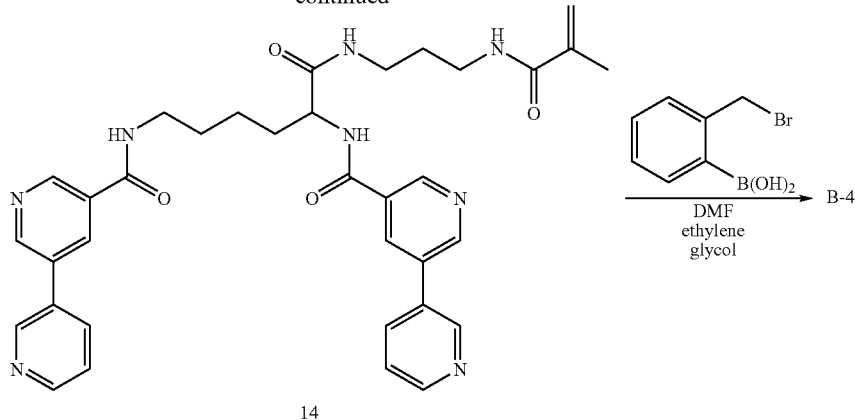

14

An extended conjugation bis viologen B-C having the generic structure shown below is disclosed in accordance with the present invention.

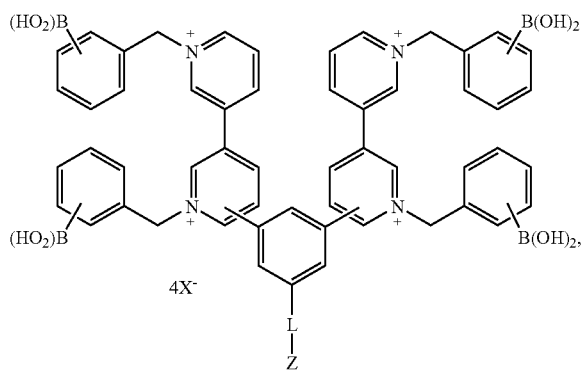

wherein

X⁻ is a counterion;

L is a divalent linking selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof;

Z is a reactive, ethylenically unsaturated group selected from but not limited to methacrylamido-, acrylamido-, methacryloyl-, acryloyl-, or styryl- optionally Z is a reactive functional group, capable of forming a covalent bond with a polymer or matrix. Such groups include but are not limited to —Br, —OH, —SH, —CO$_2$H, and —NH$_2$. In one embodiment, Z is

wherein R is H or CH$_3$;

the bond from the central benzene ring is to the ortho, meta or para position on the adjacent pyridinium rings; and —B(OH)$_2$ may be in the ortho, meta or para position.

A quencher, "B-C", having the structure below is disclosed in accordance with another preferred embodiment of the present invention.

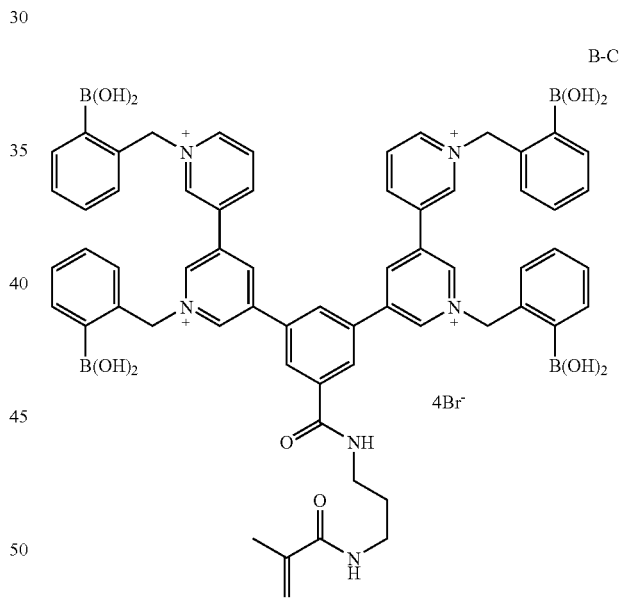

A method of making the polyviologen quencher B-C is disclosed in accordance with another embodiment of the present invention, comprising the steps of:

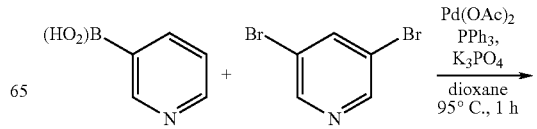

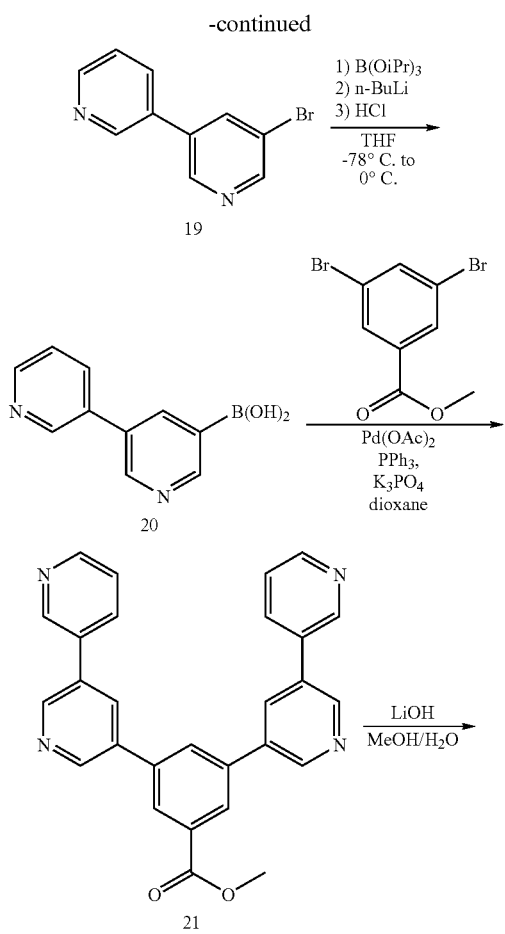
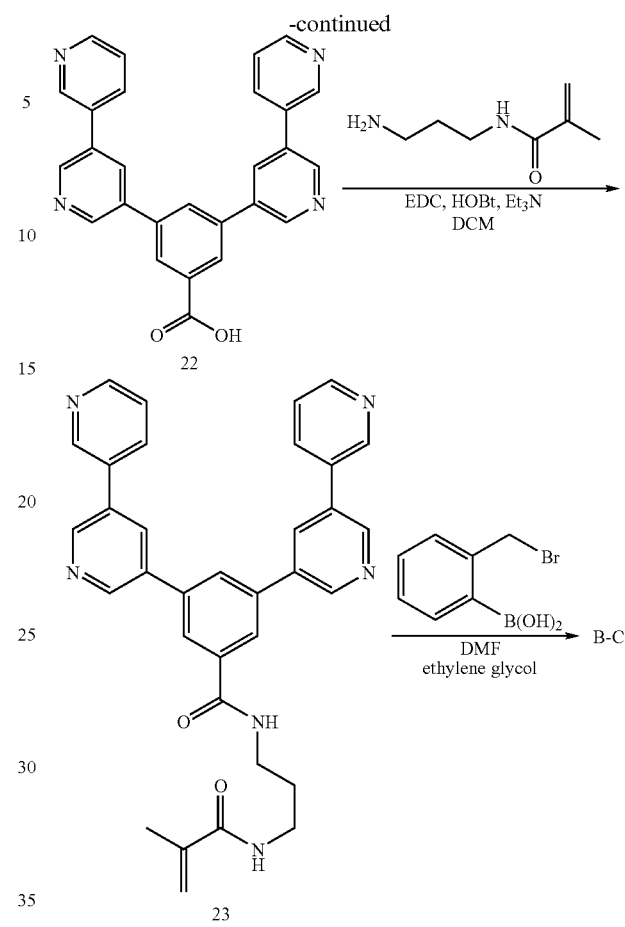
A polyviologen quencher Q having the generic structure shown below is disclosed in accordance with the preferred embodiments of the present invention.
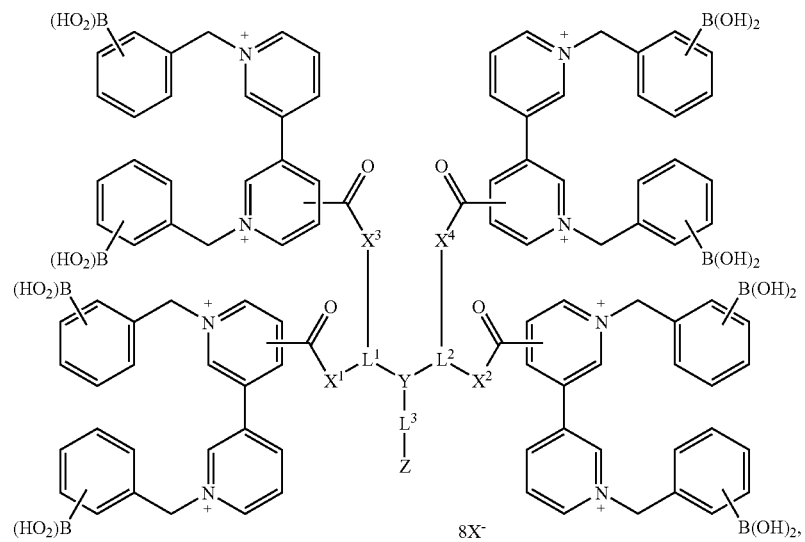

wherein

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

wherein R is H or CH$_3$;

Y is a trivalent connecting group selected from

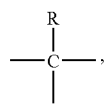

where R is H or a lower alkyl, and

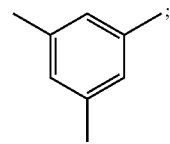

$X^-$ is a counterion;

$X^1$, $X^2$, $X^3$ and $X^4$ are —O— or —NH—; and $L^1$, $L^2$, and $L^3$ are selected from a direct bond or, a lower alkylene having 1 to 8 carbon atoms, optionally terminated with or interrupted by one or more divalent connecting groups selected from sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof.

Another polyviologen quencher, "Q-4", having the structure below is disclosed in accordance with a preferred embodiment of the present invention.

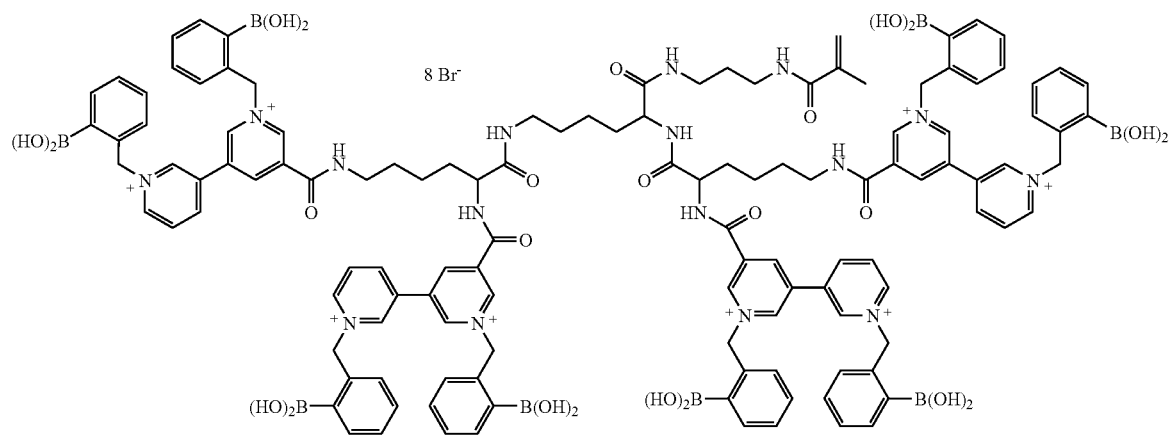

Q-4

A method of making Q-4 is disclosed in accordance with another embodiment of the present invention, wherein the method comprises the steps of:

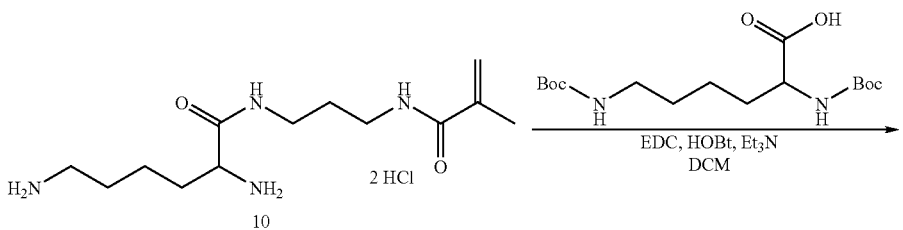

-continued

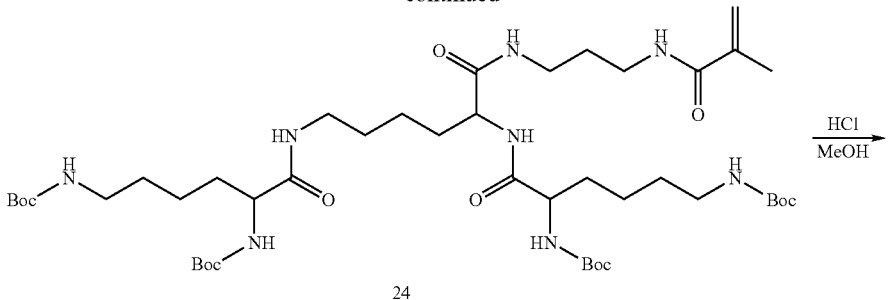
24

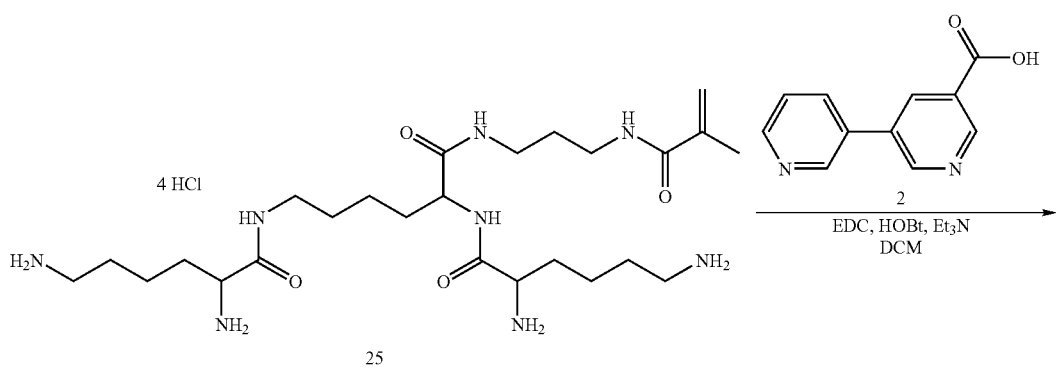
25

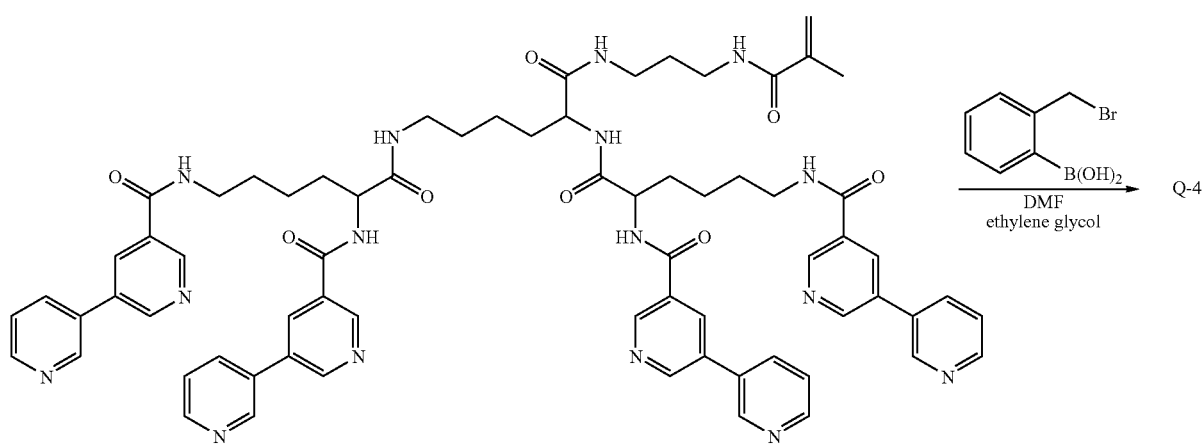
26

An analyte sensor is disclosed in accordance with one preferred embodiment of the present invention. The sensor comprises any one or more of the compounds selected from the group consisting of generic quencher, B, B-1, B-2, B-3, B-4, B-C, generic quencher Q and Q-4; and a fluophore susceptible to quenching by a viologen.

In one variation to the analyte sensor, any one or more of the compounds may be a pendant group or chain unit in a polymer.

In some embodiments, the analyte sensor is a glucose sensor. In one variation, the glucose sensor may further comprise a glucose permeable immobilizing means, e.g., a polymer matrix or a semipermeable membrane.

A composition of matter is disclosed in accordance with another preferred embodiment of the present invention. For example, the novel quenchers described above. The composition comprises a fluorophore that is susceptible to quenching by a polyviologen and a quencher comprising two or more viologen moieties, wherein each viologen moiety includes at least two boronic acid functional groups as a quencher, and a glucose permeable polymer matrix.

DETAILED DESCRIPTION OF THE PREFERRED EMBODIMENT

Definitions

Figure 1:
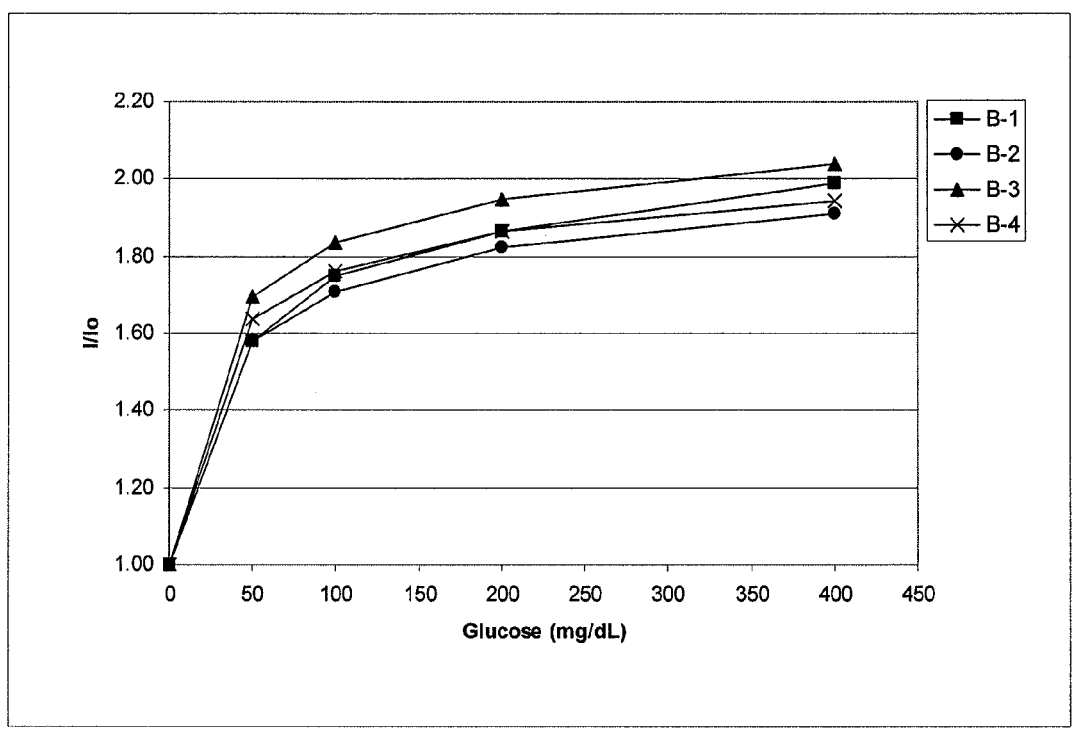
FIG. 1 illustrates the glucose response of a sensor comprising one of quenchers B-1, B-2, B-3 and B-4, and dye HPTS-triCys-MA, immobilized within a hydrogel at the tip of an optical fiber. The detection chemistry was excited at 470 nm and fluorescence was measured between 520-700 nm in the presence of increasing concentrations of glucose.

As used herein, "boronic acid" refers to a structure —B(OH)$_2$. It is recognized by those skilled in the art that a boronic acid may be present as a boronate ester at various stages in the synthesis of the quenchers of this invention. Boronic acid is meant to include such esters.

As used herein, "bis viologen" refers to compounds in which two viologens are coupled together.

"Fluorophore" refers to a substance that when illuminated by light at a particular wavelength emits light at a longer wavelength; i.e., it fluoresces. Fluorophores include organic dyes, organometallic compounds, metal chelates, fluorescent conjugated polymers, quantum dots or nanoparticles and combinations of the above. Fluorophores may be discrete moieties or substituents attached to a polymer. "Fluorescent dye" or "dye" is selected from a discrete compound or a reactive intermediate which is convertible to a second discrete compound, or to a polymerizable compound.

"Quencher" refers to a compound that reduces the emission of a fluorophore when in its presence.

"Viologen" refers generally to compounds having the basic structure of a nitrogen containing conjugated N-substituted heterocyclic aromatic bis-onium salt, such as 2,2'-, 3,3'- or 4,4'-N,N' bis-(benzyl) bipyridium dihalide (i.e., dichloride, bromide chloride), etc. Viologen also includes the substituted phenanthroline compounds.

As used herein, the term "polyviologen" refers generally to compounds comprising two or more viologen units coupled together, including bis-viologens, wherein the viologen rings are close enough that the electron affinity of the coupled compound as measured by reduction potential is enhanced over that of a single viologen.

As used herein the term "polyviologen boronic acid" refers to a polyviologen substituted with at least two boronic acid groups.

As used herein, "Linking group", also termed "L", refers to divalent moieties that covalently connect the sensing moiety to the polymer or matrix. Examples of L include those which are each independently selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH (C═O)—O—, urea —NH(C═O)NH—, thiourea —NH (C═S)—NH—, amide —(C═O)NH—, amine —NR— (where R is defined as alkyl having 1 to 6 carbon atoms) and the like.

As used herein, "coupling group" refers to a reactive group that is capable of forming a covalent bond between two viologens.

Polyviologen Boronic Acid Quenchers

In one aspect, the present invention comprises a class of fluorescence quenching compounds that are responsive to the presence of polyhydroxyl compounds such as glucose in aqueous media at or near physiological pH. In other words, the quenching efficiency is controlled by the concentration of these compounds in the medium. The quencher is comprised of two or more viologen moieties, wherein each viologen moiety is substituted with at least two boronic acid groups. In some embodiments, the adduct is immobilized in or covalently bonded to a polymer. The polyviologen quenchers, a fluorophore, and polymer may also be covalently bonded to each other.

Specific examples of the polyviologen boronic acid quenchers described herein are denoted generic B, B-1, B-2, B-3, B-4, B-C, generic Q and Q-4, and are illustrated below.

A bis-viologen quencher B, having the generic structure shown below is disclosed in accordance with the preferred embodiments of the present invention.

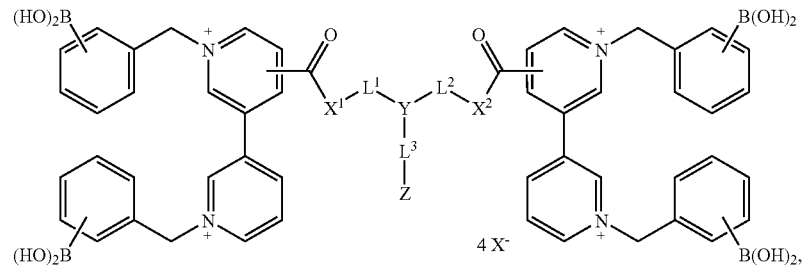

wherein

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

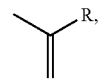

wherein R is H or CH$_3$;

Y is a trivalent connecting group selected from

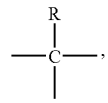

where R is H or a lower alkyl, and

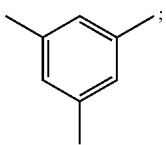

X⁻ is a counterion;

X¹ and X² are —O— or —NH—; and

L¹, L², and L³ are selected from a direct bond or, a lower alkylene having 1 to 8 carbon atoms, optionally terminated with or interrupted by one or more divalent connecting groups selected from sulfonamide (—SO₂NH—), amide —(C=O)N—, ester —(C=O)—O—, ether —O—, sulfide —S—, sulfone (—SO₂—), phenylene —C₆H₄—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof.

Some embodiments of compound B are as follows:

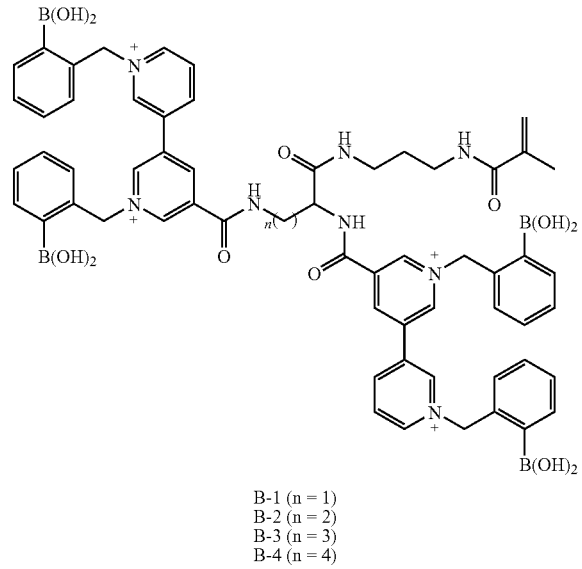

B-1 (n = 1)
B-2 (n = 2)
B-3 (n = 3)
B-4 (n = 4)

An extended conjugation bis viologen B-C having the generic structure shown below is disclosed in accordance with the present invention.

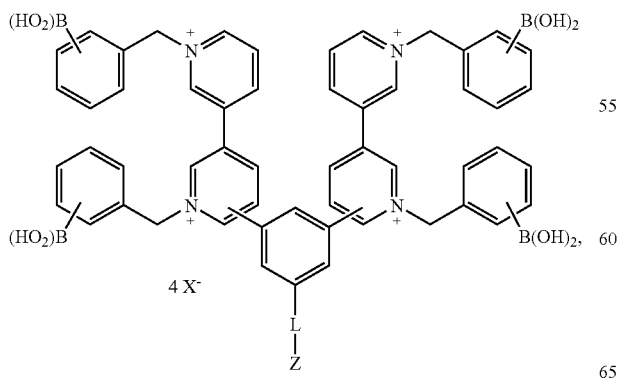

wherein

X⁻ is a counterion;

L is a divalent linking selected from a direct bond or, a lower alkylene having 1 to 8 carbon atoms, optionally terminated with or interrupted by one or more divalent connecting groups selected from sulfonamide (—SO₂NH—), amide —(C=O)N—, ester —(C=O)—O—, ether —O—, sulfide —S—, sulfone (—SO₂—), phenylene —C₆H₄—, urethane —NH(C=O)—O—, urea —NH(C=O)NH—, thiourea —NH(C=S)—NH—, amide —(C=O)NH—, amine —NR— (where R is defined as alkyl having 1 to 6 carbon atoms) or combinations thereof;

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO₂H, and —NH₂. In one embodiment, Z is

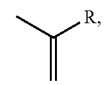

wherein R is H or CH₃;

the bond from the central benzene ring is to the ortho, meta or para position on the adjacent pyridinium rings; and —B(OH)₂ may be in the ortho, meta or para position.

One embodiment of B-C is as follows:

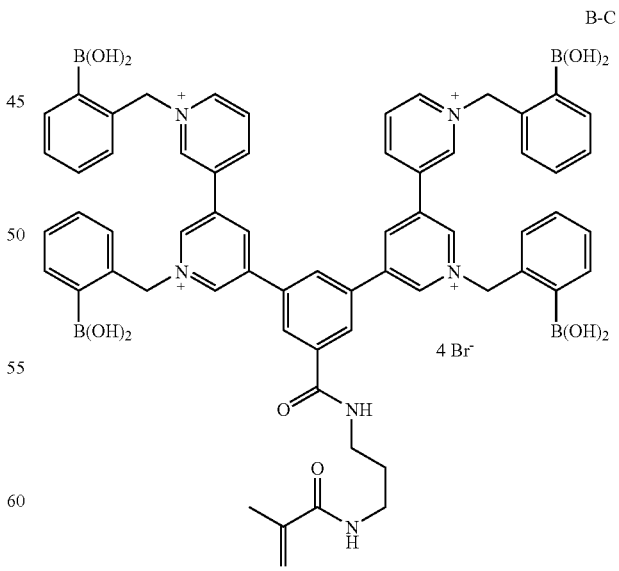

A polyviologen quencher Q having the generic structure shown below is disclosed in accordance with the preferred embodiments of the present invention.

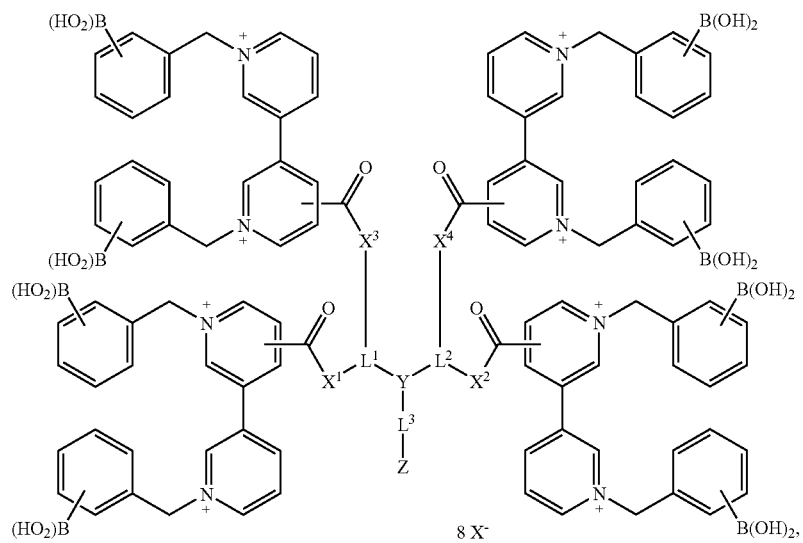

wherein

Z is a reactive, ethylenically unsaturated group selected from but not limited to methacrylamido-, acrylamido-, methacryloyl-, acryloyl-, or styryl- or optionally Z is a reactive functional group, capable of forming a covalent bond with a polymer or matrix. Such groups include but are not limited to —Br, —OH, —SH, —CO$_2$H, and —NH$_2$. In one embodiment, Z is

wherein R is H or CH$_3$;

Y is a trivalent connecting group selected from

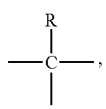

where R is H or a lower alkyl, and

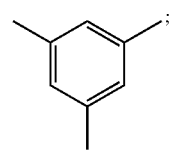

$X^-$ is a counterion;

$X^1$, $X^2$, $X^3$ and $X^4$ are —O— or —NH—; and $L^1$, $L^2$, and $L^3$ are selected from a direct bond or, a lower alkylene having 1 to 8 carbon atoms, optionally terminated with or interrupted by one or more divalent connecting groups selected from sulfonamide (—SO$_2$NH—), amide —(C═O)N—, ester —(C═O)—O—, ether —O—, sulfide —S—, sulfone (—SO$_2$—), phenylene —C$_6$H$_4$—, urethane —NH(C═O)—O—, urea —NH(C═O)NH—, thiourea —NH(C═S)—NH—, amide —(C═O)NH—, amine —NR— (where R is defined as alkyl having 1 to 6 carbon atoms) or combinations thereof.

One embodiment, termed Q-4, is as follows:

Q-4

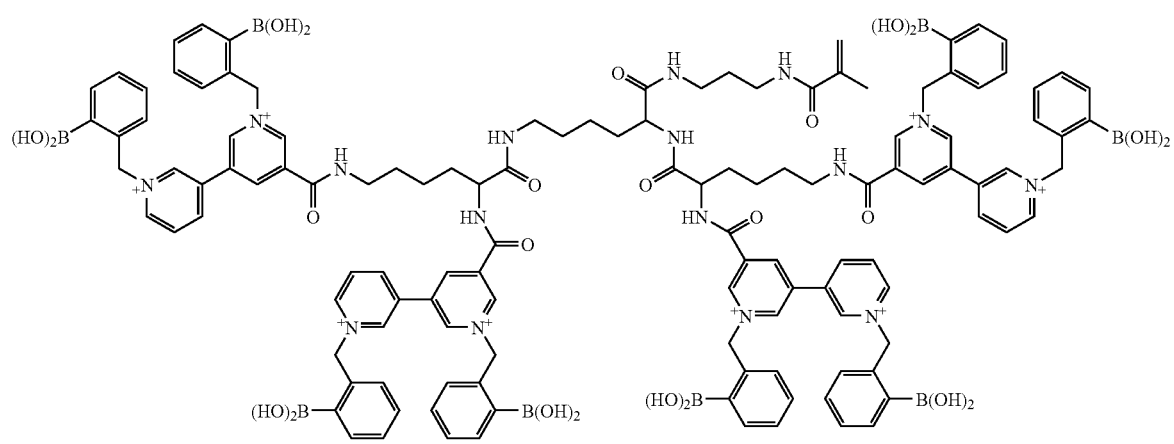

Analyte Sensors

The chemical indicator systems used in accordance with preferred embodiments of the present invention comprise a fluorophore operably coupled to an analyte binding moiety, wherein analyte binding causes an apparent optical change in the fluorophore concentration (e.g., emission intensity). Any fluophore that is quenched by the polyviologens disclosed herein may be used. Preferred fluophores bear at least one negative charge. For example, in one embodiment the fluorophore may have different acid and base forms that exhibit a detectable difference in spectral properties such that ratiometric pH sensing may be enabled; see e.g., co-pending U.S. patent application Ser. No. 11/671,880. In another embodiment, a glucose binding moiety, e.g., selected from the polyviologen boronic acid quenchers disclosed herein (B-1, B-2, B-3, B-4, B-C and Q-4), that is operably coupled to a fluorescent dye, such as HPTS-triCysMA, will quench the emission intensity of the fluorescent dye, wherein the extent of quenching is reduced upon glucose binding resulting in an increase in emission intensity related to glucose concentration. In preferred embodiments, the indicator systems comprise a dye having at least two anionic groups and a quencher having at least four boronic acids. In further preferred embodiments, the indicator systems also comprise a means for immobilizing the sensing moieties (e.g., dye-quencher) such that they remain physically close enough to one another to interact (quenching). Where in vivo sensing is desired, such immobilizing means are preferably insoluble in an aqueous environment (e.g., in vivo, intravascular), permeable to the target analytes, and impermeable to the sensing moieties. Typically, the immobilizing means comprises a water-insoluble organic polymer matrix. For example, the dye and quencher may be effectively immobilized within a DMAA (N,N-dimethylacrylamide) hydrogel matrix, which allows glucose sensing in vivo.

Some exemplary fluorophores and immobilizing means are set forth in greater detail below. In some embodiments, useful dyes include pyranine derivatives (e.g. hydroxypyrene trisulfonamide derivatives and the like), which have the following formula:

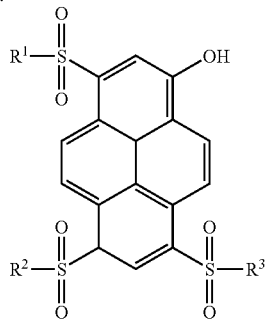

wherein $R^1$, $R^2$, $R^3$ are each $-NHR^4$, $R^4$ is $-CH_2CH_2(-OCH_2CH_2-)_nX^1$; wherein $X^1$ is $-OH$, $-OCH_3COOH$, $-CONH_2$, $-SO_3H$, $-NH_2$, or OMe; and n is between about 70 and 10,000. In one embodiment, the dyes may be bonded to a polymer through the sulfonamide functional groups.

In one preferred embodiment, the fluorescent dye may be HPTS-TriCys-MA:

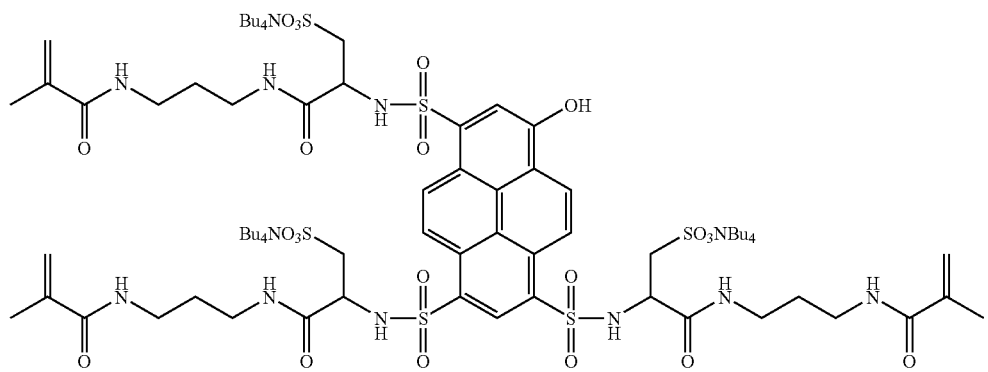

Of course, in some embodiments, substitutions other than Cys-MA on the HPTS core are consistent with aspects of the present invention, as long as the substitutions are negatively charged and have a polymerizable group. Either L or D stereoisomers of cysteine may be used. In some embodiments, only one or two of the sulfonic acids may be substituted. Likewise, in variations to HPTS-CysMA shown above, other counterions besides $NBu_4^+$ may be used, including positively charged metal ions, e.g., $Na^+$. In other variations, the sulfonic acid groups may be replaced with e.g., phosphoric, carboxylic, etc. functional groups.

In some embodiments, for use in vitro not involving a moving stream, the sensing components are used as individual (discrete) components. The dye and quencher are mixed together in liquid solution, analyte is added, the change in fluorescence intensity is measured, and the components are discarded. Polymeric matrices that can be used to trap the sensing components to prevent leaching need not be present. Optionally, the sensing components are immobilized which allows their use to measure analytes in a moving stream.

For in vivo applications, the sensor is used in a moving stream of physiological fluid which contains one or more polyhydroxyl organic compounds or is implanted in tissue such as muscle which contains said compounds. Therefore, it is preferred that none of the sensing moieties escape from the sensor assembly. Thus, for use in vivo, the sensing components are preferably part of an organic polymer sensing assembly. Soluble dyes and quenchers can be confined by a semi-permeable membrane that allows passage of the analyte but blocks passage of the sensing moieties. This can be realized by using as sensing moieties soluble molecules that are substantially larger than the analyte molecules (molecular weight of at least twice that of the analyte or greater than 1000 preferably greater than 5000); and employing a selective semipermeable membrane such as a dialysis or an ultrafiltration membrane with a specific molecular weight cutoff between the two so that the sensing moieties are quantitatively retained.

Preferably, the sensing moieties are immobilized in an insoluble polymer matrix, which is freely permeable to glucose. The polymer matrix is comprised of organic, inorganic or combinations of polymers thereof. The matrix may be composed of biocompatible materials. Alternatively, the matrix is coated with a second biocompatible polymer that is permeable to the analytes of interest.

The function of the polymer matrix is to hold together and immobilize the fluorophore and quencher moieties while at the same time allowing contact with the analyte, and binding of the analyte to the boronic acid. To achieve this effect, the matrix must be insoluble in the medium, and in close association with it by establishing a high surface area interface between matrix and analyte solution. For example, an ultra-thin film or microporous support matrix is used. Alternatively, the matrix is swellable in the analyte solution, e.g. a hydrogel matrix is used for aqueous systems. In some instances, the sensing polymers are bonded to a surface such as the surface of a light conduit, or impregnated in a microporous membrane. In all cases, the matrix must not interfere with transport of the analyte to the binding sites so that equilibrium can be established between the two phases. Techniques for preparing ultra-thin films, microporous polymers, microporous sol-gels, and hydrogels are established in the art. All useful matrices are defined as being analyte permeable.

Hydrogel polymers are used in some embodiments. The term, hydrogel, as used herein refers to a polymer that swells substantially, but does not dissolve in water. Such hydrogels may be linear, branched, or network polymers, or polyelectrolyte complexes, with the proviso that they contain no soluble or leachable fractions. Typically, hydrogel networks are prepared by a crosslinking step, which is performed on water-soluble polymers so that they swell but do not dissolve in aqueous media. Alternatively, the hydrogel polymers are prepared by copolymerizing a mixture of hydrophilic and crosslinking monomers to obtain a water swellable network polymer. Such polymers are formed either by addition or condensation polymerization, or by combination process. In these cases, the sensing moieties are incorporated into the polymer by copolymerization using monomeric derivatives in combination with network-forming monomers. Alternatively, reactive moieties are coupled to an already prepared matrix using a post polymerization reaction. Said sensing moieties are units in the polymer chain or pendant groups attached to the chain.

The hydrogels useful in this invention are also monolithic polymers, such as a single network to which both dye and quencher are covalently bonded, or multi-component hydrogels. Multi-component hydrogels include interpenetrating networks, polyelectrolyte complexes, and various other blends of two or more polymers to obtain a water swellable composite, which includes dispersions of a second polymer in a hydrogel matrix and alternating microlayer assemblies.

Monolithic hydrogels are typically formed by free radical copolymerization of a mixture of hydrophilic monomers, including but not limited to HEMA, PEGMA, methacrylic acid, hydroxyethyl acrylate, N-vinyl pyrrolidone, acrylamide, N,N'-dimethyl acrylamide, and the like; ionic monomers include methacryloylaminopropyl trimethylammonium chloride, diallyl dimethyl ammonium. chloride, vinyl benzyl trimethyl ammonium chloride, sodium sulfopropyl methacrylate, and the like; crosslinkers include ethylene dimethacrylate, PEGDMA, methylene bis-acrylamide, methylene bis-methacrylamide, trimethylolpropane triacrylate, and the like. The ratios of monomers are chosen to optimize network properties including permeability, swelling index, and gel strength using principles well established in the art. The concentration of dye is chosen to optimize emission intensity. The ratio of quencher to dye is adjusted to provide sufficient quenching to produce the desired measurable signal.

In one embodiment, the glucose sensors of the invention comprise a fluorophore that is susceptible to quenching by a polyviologen and a quencher comprising two or more viologen moieties, wherein each viologen moiety includes at least two boronic acid functional groups, and a glucose permeable polymer matrix.

Example 1

SYNTHESIS OF B-1, B-2, B-3 AND B-4 (SCHEME 1)

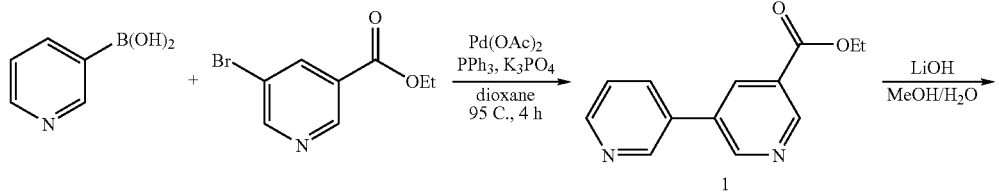

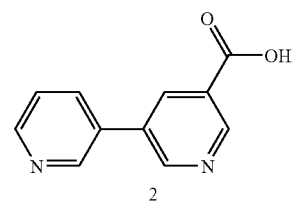

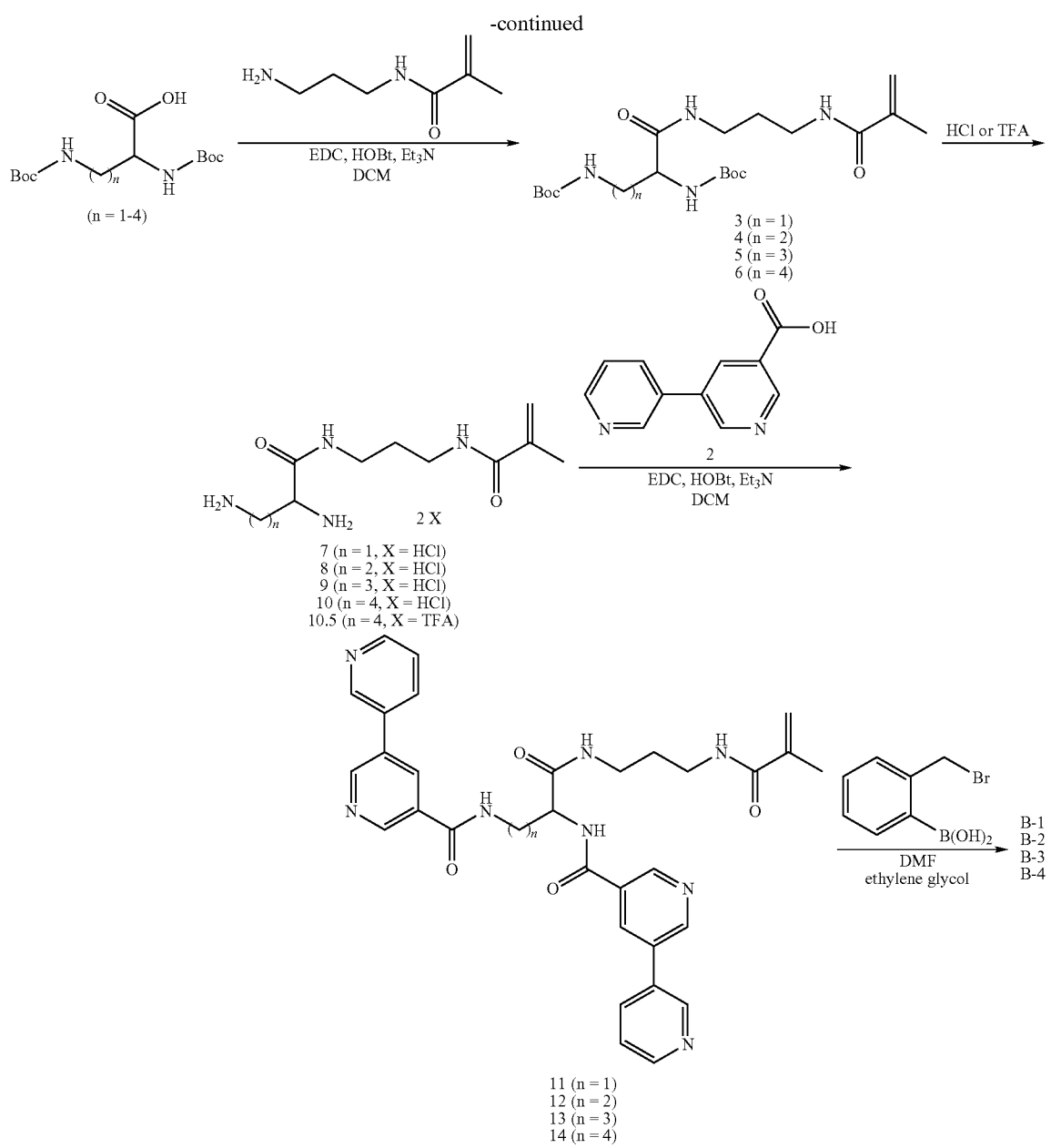

Referring to Scheme 1 (synthesis of B-1, B-2, B-3 and B-4), synthesis of compound 2, to a 500-mL oven-dried round-bottomed flask with a sidearm and condenser, was added ethyl-5-bromonicotinate (38.0 g, 0.17 mol), 3-pyridineboronic acid (22.5 g, 0.18 mol), and anhydrous 1,4-dioxane (220 mL) under argon. An aqueous solution of $K_3PO_4$ (2 M, 182 mL) was added, followed by the addition of $Pd(OAc)_2$ (1.86 g, 8.3 mmol) and $PPh_3$ (8.7 g, 33.0 mmol). The reaction was refluxed for 2 h. while a gentle and steady stream of argon was bubbled through the solution. After cooling to room temperature, the $POPh_3$ crystals which formed were filtered from the biphasic reaction mixture. The aqueous layer was extracted with EtOAc (3×200 mL). The combined organic layers were washed with brine (1×200 mL), dried over $MgSO_4$, and evaporated under reduced pressure until ~50 mL remained. To this crude mixture of 1, was added methanol (25 mL) and water (20 mL). After cooling to 0° C., LiOH (8.0 g, 0.33 mmol) was added, and the reaction was stirred for 30 min. at room temperature. The organics were evaporated under reduced pressure. The remaining basic aqueous phase was diluted with water (50 mL) and washed with EtOAc several times until the EtOAc washes remained colorless. The basic water was acidified with $KHSO_4$ (1M) until pH-4. The white precipitate (compound 2) which formed was collected by filtration, washed with water, acetone, and air dried. Further drying under reduced pressure yielded 20.3 g (61%) of white powder. $^1$H NMR (CD$_3$OD, 500 MHz) δ 7.61 (ddd, J=8.0, 5.0, 0.77 Hz, 1H), 8.23 (ddd, J=8.0, 2.3, 1.6 Hz, 1H), 8.64 (dd, J=5.0, 1.5 Hz, 1H), 8.65 (t, J=2.0 Hz, 1H), 8.92 (dd, J=2.3, 0.66 Hz, 1H), 9.04 (d, J=2.3 Hz, 1H), 9.17 (d, J=2.0 Hz, 1H).

Referring to Scheme 1, synthesis of compounds 3 and 7, to a cooled (0° C.) solution of N,N-di-boc-diaminopropionic acid (dicyclohexylammonium) salt (1 g, 2.1 mmol) in dichloromethane (75 mL), was added N-(3-dimethylaminopropyl)-N'-ethylcarbodiimide hydrochloride (0.47 g, 2.5 mmol), 1-hydroxy-benzotriazole hydrate (0.33 g, 2.5 mmol), and triethylamine (0.35 mL, 2.5 mmol). After stirring for 30 min. at 0° C., N-(3-aminopropyl)methacrylamide hydrochloride (0.44 g, 2.5 mmol) and triethylamine (0.35 mL, 2.5 mmol) were added. The reaction was stirred for 8 h., then washed with saturated NaHCO$_3$ (3×25 mL). The DCM layer was dried with MgSO$_4$, reduced in volume in vacuo, and purified by flash column chromatography (2%-20% methanol in DCM) to give compound 3. TLC: R$_f$=0.68 (10% MeOH/DCM). The appropriate fractions were pooled and concentrated to about 5 mL (not taken to dryness to avoid polymerization), then 1.25 M methanolic HCl (20 mL) was added and the reaction was stirred for 18 h., and concentrated in vacuo to give 7 as a white foam (0.5 g, 81%). $^1$H NMR (D$_2$O, 500 MHz) δ 1.79 (p, J=6.8 Hz, 2H), 1.92 (s, 3H), 3.29 (m, 5H), 3.42 (dd, J=14, 6.6 Hz, 1H), 3.51 (dd, J=14, 5.5 Hz, 1H), 4.18 (t, J=6.1 Hz, 1H), 5.44 (s, 1H), 5.68 (s, 1H).

Referring to Scheme 1, synthesis of compounds 4 and 8, to a cooled (0° C.) solution of N,N-di-boc-diaminobutyric acid (dicyclohexylammonium) salt (1 g, 2.0 mmol) in dichloromethane (75 mL), was added N-(3-dimethylaminopropyl)-N'-ethylcarbodiimide hydrochloride (0.47 g, 2.47 mmol), 1-hydroxy-benzotriazole hydrate (0.33 g, 2.47 mmol), and triethylamine (0.33 mL, 2.4 mmol). After stirring for 30 min. at 0° C., N-(3-aminopropyl)methacrylamide hydrochloride (0.43 g, 2.4 mmol) and triethylamine (0.33 mL, 2.4 mmol) were added. The reaction was stirred for 18 h., then washed with saturated NaHCO$_3$ (3×25 mL). The DCM layer was dried with MgSO$_4$, reduced in volume in vacuo, and purified by flash column chromatography (2%-20% methanol in DCM) to give compound 4 (0.85 g, 96%), which was then dissolved in 1.25 M methanolic HCl (20 mL) and stirred for 18 h. Concentration in vacuo to gave 8 as a white foam (0.5 g). $^1$H NMR (D2O, 500 MHz) δ 1.79 (p, J=6.9 Hz, 2H), 1.92 (s, 3H), 2.26 (m, 2H), 3.11 (m, 2H), 3.29 (m, 4H), 4.07 (t, J=6.7 Hz, 1H), 5.44 (s, 1H), 5.68 (s, 1H).

Referring to Scheme 1, synthesis of compounds 5 and 9, to a cooled (0° C.) solution of N,N-di-boc-ornithine (1 g, 3.0 mmol) in dichloromethane (70 mL), was added N-(3-dimethylaminopropyl)-N'-ethylcarbodiimide hydrochloride (0.7 g, 3.6 mmol), 1-hydroxy-benzotriazole hydrate (0.49 g, 3.6 mmol), and triethylamine (0.5 mL, 3.6 mmol). After stirring for 30 min. at 0° C., N-(3-aminopropyl)methacrylamide hydrochloride (0.64 g, 3.6 mmol) and triethylamine (0.5 mL, 3.6 mmol) were added. The reaction was stirred for 16 h., then washed with saturated NaHCO$_3$ (3×25 mL). The DCM layer was dried with MgSO$_4$, reduced in volume in vacuo, and purified by flash column chromatography (2%-20% methanol in DCM) to give compound 5. TLC: R$_f$=0.70 (10% MeOH/DCM). The appropriate fractions were pooled and concentrated to about 5 mL (not taken to dryness to avoid polymerization), then 1.25 M methanolic HCl (20 mL) was added and the reaction was stirred for 18 h., and concentrated in vacuo to give 9 as a white foam (0.9 g, 92%). $^1$H NMR (D$_2$O, 500 MHz) δ 1.76 (m, 4H), 1.92 (s, 3H), 1.95 (m, 2H), 3.04 (t, J=7.6 Hz, 2H), 3.29 (m, 4H), 3.99 (t, J=6.7 Hz, 1H), 5.44 (s, 1H), 5.68 (s, 1H).

Referring to Scheme 1, synthesis of compounds 6 and 10, to a cooled (0° C.) solution of N,N-di-boc-lysine (dicyclohexylammonium) salt (4.2 g, 8.0 mmol) in dichloromethane (200 mL), was added N-(3-dimethylaminopropyl)-N'-ethylcarbodiimide hydrochloride (1.8 g, 9.6 mmol), 1-hydroxy-benzotriazole hydrate (1.3 g, 9.6 mmol), and triethylamine (1.3 mL, 9.6 mmol). After stirring for 30 min. at 0° C., N-(3-aminopropyl)methacrylamide hydrochloride (1.7 g, 9.6 mmol) and triethylamine (1.3 mL, 9.6 mmol) were added. The reaction was stirred for 8 h., then washed with saturated NaHCO3 (3×75 mL). The DCM layer was dried with MgSO$_4$, reduced in volume in vacuo, and purified by flash column chromatography (2%-20% methanol in DCM) to give compound 6. TLC: R$_f$=0.71 (10% MeOH/DCM). The appropriate fractions were pooled and concentrated to about 5 mL (not taken to dryness to avoid polymerization), then 1.25 M methanolic HCl (30 mL) was added and the reaction was stirred for 48 h., and concentrated in vacuo to give 10 as a white foam (2.1 g, 78%). $^1$H NMR (D2O, 500 MHz) δ 1.44 (p, J=8.3 Hz, 2H), 1.71 (p, J=7.8 Hz, 2H), 1.78 (p, J=6.9 Hz, 2H), 1.90 (m, 2H), 1.92 (s, 3H), 3.00 (t, J=7.7 Hz, 2H), 3.29 (m, 4H), 3.95 (t, J=6.7 Hz, 1H), 5.44 (s, 1H), 5.67 (s, 1H).

Referring to Scheme 1, synthesis of compound 10.5, to a cooled (0° C.) solution of N,N-di-boc-lysine (dicyclohexylammonium) salt (2.1 g, 4.0 mmol) in dichloromethane (150 mL), was added N-(3-dimethylaminopropyl)-N'-ethylcarbodiimide hydrochloride (0.92 g, 4.8 mmol), 1-hydroxy-benzotriazole hydrate (0.65 g, 4.8 mmol), and triethylamine (1.3 mL, 9.6 mmol). After stirring for 40 min. at 0° C., N-(3-aminopropyl)methacrylamide hydrochloride (0.86 g, 4.8 mmol) was added. The reaction was stirred for 3 h., then washed with saturated NaHCO$_3$ (3×25 mL). The DCM layer was dried with MgSO$_4$, reduced in volume in vacuo, and purified by flash column chromatography (2%-20% methanol in DCM) to give compound 6. TLC: R$_f$=0.71 (10% MeOH/DCM). The appropriate fractions were pooled and concentrated to about 10 mL (not taken to dryness to avoid polymerization), then trifluoroacetic acid (10 mL) was added at 0° C. and the reaction was stirred for 45 min., and purified by flash column chromatography (30% methanol in DCM).

Referring to Scheme 1, synthesis of compound 11, to a cooled (0° C.) suspension of compound 2 (1 g, 5 mmol) in dichloromethane (100 mL), was added N-(3-dimethylaminopropyl)-N'-ethylcarbodiimide hydrochloride (1.2 g, 6 mmol), 1-hydroxy-benzotriazole hydrate (0.81 g, 6 mmol), and triethylamine (0.8 mL, 5.7 mmol). After stirring for 30 min. at 0° C. (the reaction became almost clear), compound 7 (0.5 g, 1.7 mmol) and triethylamine (0.6 mL, 4.3 mmol) were added. The reaction was stirred for 18 h., then washed with saturated NaHCO$_3$ (3×75 mL). The DCM layer was dried with MgSO$_4$, reduced in volume in vacuo, and purified by flash column chromatography (2%-20% methanol in DCM) to give compound 11 (50 mg, 5%). TLC: R$_f$=0.3 (20% MeOH/DCM). $^1$H NMR (CDCl$_3$, 500 MHz) δ 1.70 (p, J=6.1 Hz, 2H), 1.88 (s, 3H), 3.22 (m, 1H), 3.33 (m, 1H), 3.40 (m, 2H), 3.96 (dt, J=14.2, 5.5 Hz, 1H), 4.20 (ddd, J=14.3, 6.3, 3.1 Hz, 1H), 4.83 (m, 1H), 5.29 (m, 1H), 5.63 (m, 1H), 6.11 (t, J=6.5 Hz, 1H), 7.34 (t, 1H), 7.44 (m, 2H), 7.94 (m, 1H), 7.99 (m, 1H), 8.06 (t, 1H), 8.45 (t, J=2.2 Hz, 1H), 8.52 (t, J=2.2 Hz, 1H), 8.70 (m, 2H), 8.85 (d, 1H), 8.88 (d, J=1.7 Hz, 1H), 8.95 (d, J=1.7 Hz, 1H), 8.99 (d, J=2.2 Hz, 1H), 9.01 (d, J=2.2 Hz, 1H), 9.13 (d, J=2.1 Hz, 1H), 9.23 (d, J=2.1 Hz, 1H).

Referring to Scheme 1, synthesis of compound 12, to a cooled (0° C.) suspension of compound 2 (0.5 g, 2.4 mmol) in dichloromethane (50 mL), was added N-(3-dimethylaminopropyl)-N'-ethylcarbodiimide hydrochloride (0.56 g, 2.9 mmol), 1-hydroxy-benzotriazole hydrate (0.4 g, 2.9 mmol), and triethylamine (0.5 mL, 3.6 mmol). After stirring for 30 min. at 0° C. (the reaction became almost clear), compound 8 (0.25 g, 0.8 mmol) and triethylamine (1.0 mL, 7.2 mmol) were added. The reaction was stirred for 24 h., then washed with saturated NaHCO$_3$ (3×50 mL). The DCM layer was dried with MgSO$_4$, reduced in volume in vacuo, and purified by flash column chromatography (2%-30% methanol in DCM) to give compound 12 (0.14 g, 29%). $^1$H NMR (CDCl$_3$, 500 MHz) δ 1.69 (p, J=5.8 Hz, 2H), 1.89 (s, 3H), 2.24 (p, J=7.4 Hz, 2H), 3.26 (m, 1H), 3.35 (m, 4H), 4.04 (m, 1H), 4.84 (q, J=6.8 Hz, 1H), 5.30 (s, 1H), 5.67 (s, 1H), 6.32 (t, J=6.4 Hz, 1H), 7.44 (m, 2H), 7.72 (t, J=6.4 Hz, 1H), 7.89 (m, 2H), 7.96 (m, 2H), 8.45 (t, J=2.1 Hz, 1H), 8.47 (t, J=2.2 Hz, 1H), 8.69 (m, 2H), 8.91 (d, J=1.8 Hz, 1H), 8.92 (d, J=1.7 Hz, 1H), 8.96 (d, J=2.2 Hz, 1H), 8.99 (d, J=2.2 Hz, 1H), 9.14 (d, J=2.1 Hz, 1H), 9.17 (d, J=2.1 Hz, 1H).

Referring to Scheme 1, synthesis of compound 13, to a cooled (0° C.) suspension of compound 2 (0.6 g, 3.0 mmol) in dichloromethane (100 mL), was added N-(3-dimethylaminopropyl)-N'-ethylcarbodiimide hydrochloride (0.69 g, 3.6 mmol), 1-hydroxy-benzotriazole hydrate (0.49 g, 3.6 mmol), and triethylamine (0.5 mL, 3.6 mmol). After stirring for 30 min. at 0° C. (the reaction became almost clear), compound 9 (0.4 g, 1.2 mmol) and triethylamine (1.0 mL, 7.2 mmol) were added. The reaction was stirred for 16 h., then washed with saturated NaHCO$_3$ (3×50 mL). The DCM layer was dried with MgSO$_4$, reduced in volume in vacuo, and purified by flash column chromatography (2%-25% methanol in DCM) to give compound 13 (90 mg, 12%). $^1$H NMR (CDCl$_3$, 500 MHz) δ 1.70 (m, 2H), 1.75 (m, 2H), 1.87 (m, 2H), 1.89 (s, 3H), 1.98 (m, 1H), 2.14 (m, 1H), 3.28 (m, 1H), 3.35 (m, 1H), 3.40 (m, 2H), 3.64 (m, 1H), 3.70 (m, 1H), 4.85 (q, J=4.9 Hz, 1H), 5.30 (s, 1H), 5.67 (s, 1H), 6.40 (t, J=5.0 Hz, 1H), 7.36 (t, J=5.0 Hz, 1H), 7.42 (dd, J=3.9, 2.2 Hz, 1H), 7.43 (dd, J=3.9, 2.2 Hz, 1H), 7.65 (t, J=4.45 Hz, 1H), 7.72 (d, J=6.1 Hz, 1H), 7.93 (d, J=1.5 Hz, 1H), 7.95 (d, J=1.5 Hz, 1H), 8.42 (m, 2H), 8.67 (dd, J=4.1, 1.0 Hz, 1H), 8.68 (dd, J=4.0, 1.2 Hz, 1H), 8.889 (s, 1H), 8.891 (s, 1H), 8.93 (d, J=1.7 Hz, 1H), 8.96 (d, J=1.8 Hz, 1H), 9.10 (d, J=1.6 Hz, 1H), 9.13 (d, J=1.7 Hz, 1H).

Referring to Scheme 1, synthesis of compound 14, to a cooled (0° C.) suspension of compound 2 (1 g, 5.0 mmol) in dichloromethane (150 mL), was added N-(3-dimethylaminopropyl)-N'-ethylcarbodiimide hydrochloride (1.2 g, 6.0 mmol), 1-hydroxy-benzotriazole hydrate (0.81 g, 6.0 mmol), and triethylamine (0.83 mL, 6.0 mmol). After stirring for 30 min. at 0° C. (the reaction became clear yellow), a solution of compound 10.5 (1 g, 2.0 mmol) in DMF (3 mL), and triethylamine (0.56 mL, 4.0 mmol) were added. The reaction was stirred at room temperature for 5 h., then washed with saturated NaHCO$_3$ (3×75 mL). The DCM layer was dried with MgSO$_4$, reduced in volume in vacuo, and purified by flash column chromatography (2%-20% methanol in DCM) to give compound 14 (0.3 g, 24%). $^1$H NMR (CDCl$_3$, 500 MHz) δ 1.59 (m, 2H), 1.70 (m, 2H), 1.79 (m, 2H), 1.91 (s, 3H), 1.96 (m, 1H), 2.05 (m, 1H), 3.35 (m, 4H), 3.52 (m, 1H), 3.61 (m, 1H), 4.70 (q, J=7.6 Hz, 1H), 5.31 (s, 1H), 5.69 (s, 1H), 6.41 (t, J=6.1 Hz, 1H), 7.23 (m, 2H), 7.41 (m, 2H), 7.52 (d, J=2.2 Hz, 1H), 7.90 (m, 2H), 8.35 (t, J=2.2 Hz, 1H), 8.38 (t, J=2.2 Hz, 1H), 8.66 (t, J=1.5 Hz, 1H), 8.67 (t, J=1.5 Hz, 1H), 8.85 (t, J=1.8 Hz, 2H), 8.88 (d, J=2.2 Hz, 1H), 8.89 (d, J=2.2 Hz, 1H), 9.03 (d, J=2.0 Hz, 1H), 9.11 (d, J=2.1 Hz, 1H).

Referring to Scheme 1, synthesis of B-1,2-Bromomethylphenyl boronic acid (0.11 g, 0.5 mmol) was added to a solution of compound 11 (50 mg, 84 µmol) in DMF (2 mL) and ethylene glycol (28 µL, 0.5 mmol). The reaction was stirred at 55° C. for 72 h. Diethylether (20 mL) was added to separate the product as an oil. The solvent was decanted, and the remaining oil was sonicated in acetone until it became a pale yellow powder. The solid was collected by centrifugation, washed with acetone several times and dried under argon (95 mg, 79%). $^1$H NMR (D$_2$O, 500 MHz) δ 1.69 (p, J=6.6 Hz, 2H), 1.76 (s, 3H), 3.14 (m, 2H), 3.23 (m, 3H), 3.96 (m, 2H), 5.29 (s, 1H), 5.50 (s, 1H), 6.06 (s, 4H), 6.11 (s, 2H), 6.12 (s, 2H), 7.55 (m, 2H), 7.75 (m, 4H), 8.21 (d, J=6.3 Hz, 1H), 8.23 (d, J=6.3 Hz, 1H), 8.86 (m, 2H), 9.04 (m, 2H), 9.20 (m, 3H), 9.27 (s, 1H), 9.32 (s, 1H), 9.35 (s, 1H), 9.37 (s, 1H), 9.41 (s, 1H), 9.44 (s, 1H).

Referring to Scheme 1, synthesis of B-2,2-Bromomethylphenyl boronic acid (0.30 g, 1.4 mmol) was added to a solution of compound 12 (0.14 g, 0.23 mmol) in DMF (2 mL) and ethylene glycol (80 µL, 1.4 mmol). The reaction was stirred at 55° C. for 72 h. Diethylether (20 mL) was added to separate the product as an oil. The solvent was decanted, and the remaining oil was sonicated in acetone until it became a pale yellow powder. The solid was collected by centrifugation, washed with acetone several times and dried under argon (0.16 g, 47%).

Referring to Scheme 1, synthesis of B-3, 2-Bromomethylphenyl boronic acid (0.20 g, 0.87 mmol) was added to a solution of compound 13 (90 mg, 0.14 mmol) in DMF (2 mL) and ethylene glycol (50 µL, 0.87 mmol). The reaction was stirred at 55° C. for 72 h. Diethylether (20 mL) was added to separate the product as an oil. The solvent was decanted, and the remaining oil was sonicated in acetone until it became a pale yellow powder. The solid was collected by centrifugation, washed with acetone several times and dried under argon (0.13 g, 65%).

Referring to Scheme 1, synthesis of B-4,2-Bromomethylphenyl boronic acid (0.60 g, 2.8 mmol) was added to a solution of compound 14 (0.3 g, 0.47 mmol) in DMF (2 mL) and ethylene glycol (0.23 mL, 4.0 mmol). The reaction was stirred at 60° C. for 72 h. Diethylether (20 mL) was added to separate the product as an oil. The solvent was decanted, and the remaining oil was sonicated in acetone until it became a pale yellow powder. The solid was collected by centrifugation, washed with acetone several times and dried under argon (0.38 g, 54%).

Example 2

ALTERNATE SYNTHESIS OF B-4 (SCHEME 2)

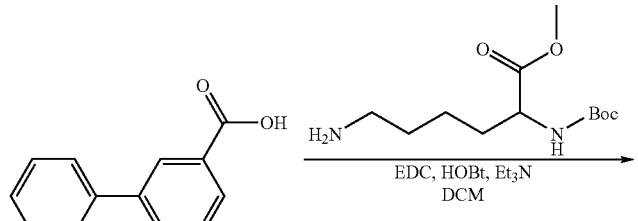

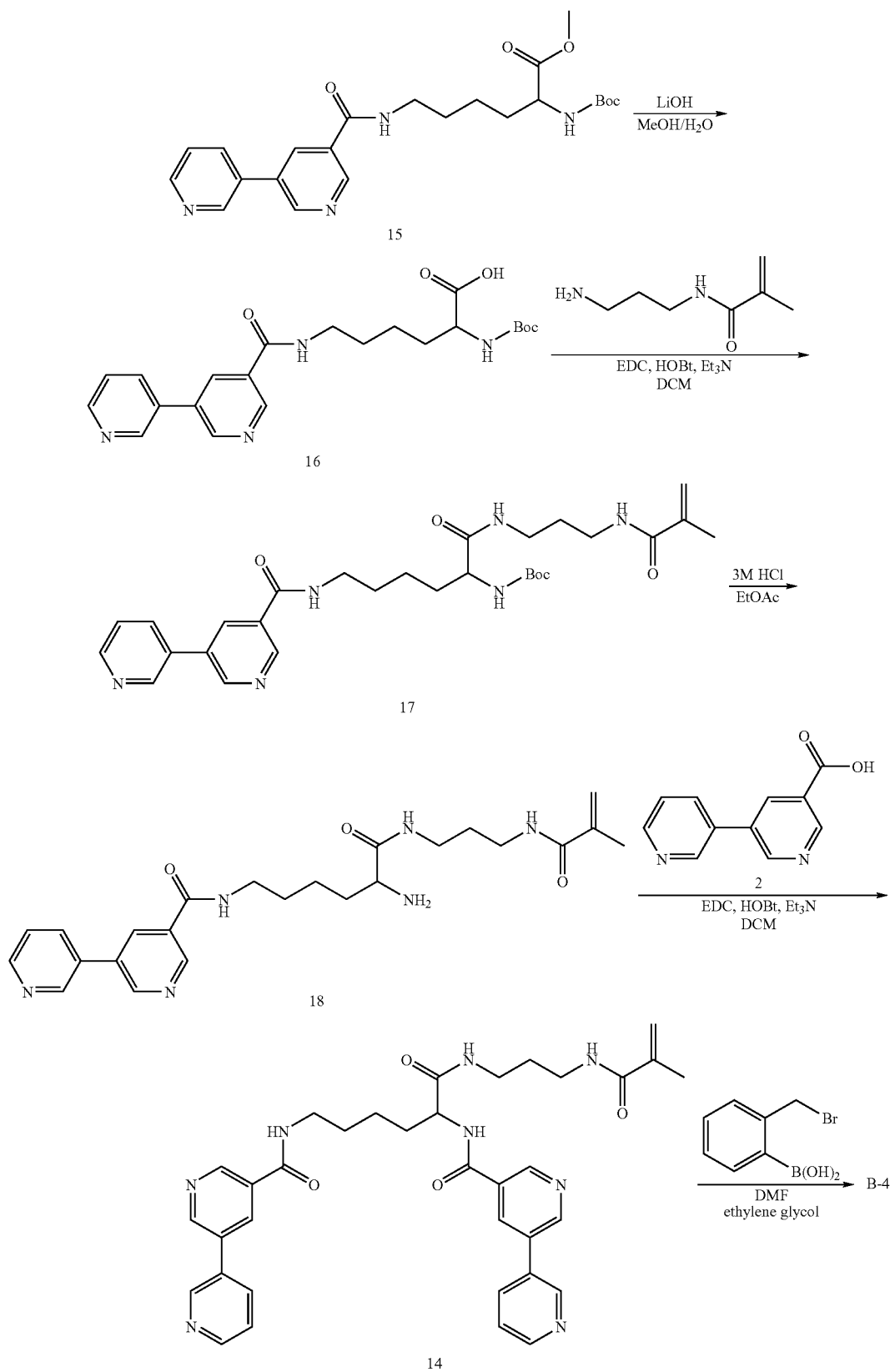

Referring to Scheme 2 (alternate synthesis of B-4), synthesis of compound 15, to a cooled (0° C.) suspension of compound 2 (0.40 g, 2.0 mmol) in dichloromethane (20 mL), was added N-(3-dimethylaminopropyl)-N'-ethylcarbodiimide hydrochloride (0.46 g, 2.4 mmol), 1-hydroxy-benzotriazole hydrate (0.32 g, 2.4 mmol), and triethylamine (0.67 mL, 4.8 mmol). After stirring for 10 min. at 0° C. (the reaction became clear), a solution of Nα-boc-lysine methyl ester acetate salt (0.62 g, 2.4 mmol) in DCM (6 mL) was added. The reaction was stirred while warming to room temperature for 16 h., then washed with saturated NaHCO₃ (2×10 mL). The DCM layer was dried with MgSO₄, reduced in volume in vacuo, and purified by flash column chromatography (2%-20% methanol in DCM) to give compound 15 (0.22 g, 25%).

Referring to Scheme 2, synthesis of compound 16, to a cooled (0° C.) solution of compound 15 (0.37 g, 0.84 mmol) in methanol (15 mL) and water (5 mL), was added LiOH (0.6 g, 2.5 mmol), and the reaction was stirred at room temperature for 16 h. The methanol was evaporated in vacuo, and the pH of the remaining water was adjusted to pH~5 with 3 M HCl. The aqueous solution was extracted with DCM (5×10 mL). The DCM layers were dried with MgSO₄ and evaporated to a foam (0.28 g, 78%).

Referring to Scheme 2, synthesis of compound 17, to a cooled (0° C.) solution of compound 16 (0.28 g, 0.65 mmol) in dichloromethane (75 mL), was added N-(3-dimethylaminopropyl)-N'-ethylcarbodiimide hydrochloride (0.15 g, 0.78 mmol), 1-hydroxy-benzotriazole hydrate (0.11 g, 0.78 mmol), and triethylamine (0.22 mL, 1.57 mmol). After stirring for 15 min. at 0° C., N-(3-aminopropyl)methacrylamide hydrochloride (0.14 g, 0.78 mmol) was added. The reaction was stirred for 24 h., then washed with saturated NaHCO₃ (2×50 mL). The DCM layer was dried with MgSO₄, reduced in volume in vacuo, and purified by flash column chromatography (2%-20% methanol in DCM) to give compound 17.

Referring to Scheme 2, synthesis of compound 18, to a suspension of compound 17 (0.45 g, 0.81 mmol) in ethyl acetate was added concentrated HCl (3 mL). After stirring for 20 min., the volatiles were removed in vacuo. The remaining acidic solution was neutralized with 3 M NaOH, and lyophilized for 16 h. The resulting white solid was sonicated in DCM for 2 h. The insolubles were filtered, and the filtrate was concentrated in vacuo to a clear foam (0.28 g, 76%).

Referring to Scheme 2, synthesis of compound 14, to a cooled (0° C.) solution of compound 2 (0.10 g, 0.52 mmol) in dichloromethane (10 mL), was added N-(3-dimethylaminopropyl)-N'-ethylcarbodiimide hydrochloride (0.12 g, 0.62 mmol), 1-hydroxy-benzotriazole hydrate (0.08 g, 0.62 mmol), and triethylamine (0.17 mL, 1.24 mmol). After stirring for 10 min. at 0° C., a solution of compound 18 (0.28 g, 0.62 mmol) in DCM (10 mL) was added. The reaction was stirred for 24 h., then washed with saturated NaHCO₃ (2×50 mL). The DCM layer was dried with MgSO₄, reduced in volume in vacuo, and purified by flash column chromatography (2%-20% methanol in DCM) to give compound 14 (70 mg, 23%).

Example 3

SYNTHESIS OF B-C (SCHEME 3)

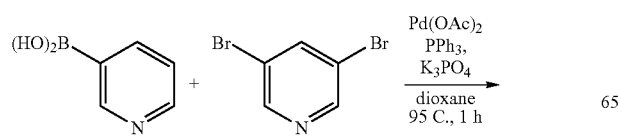

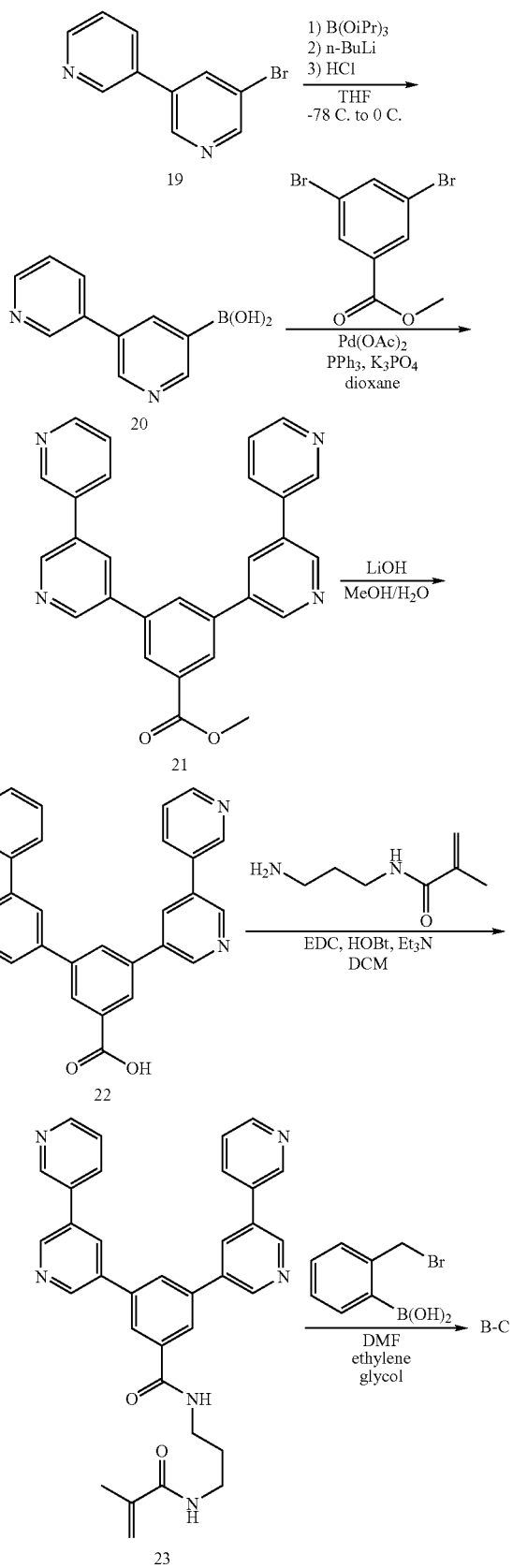

Referring to Scheme 3 (synthesis of B-C), synthesis of compound 19, to a suspension of 3,5-dibromopyridine (2.1 g, 9.0 mmol) and 3-pyridineboronic acid (1.1 g, 9.0 mmol) in anhydrous 1,4-dioxane (40 mL), was added an aqueous solution of $K_3PO_4$ (2 M, 9 mL), followed by $PPh_3$ (0.5 g, 2.0 mmol) and $Pd(OAc)_2$ (0.11 g, 0.5 mmol). The reaction was refluxed for 2 h. while a gentle and steady stream of argon was bubbled through the solution. After cooling to room temperature, the aqueous layer was extracted with EtOAc (1×100 mL). The organic layer was washed with dilute $NaHCO_3$ (3×50 mL) and brine (1×50 mL), dried over $MgSO_4$, concentrated in vacuo, and purified by flash column chromatography (2%-20% methanol in DCM) to give compound 19 (1.3 g, 61%). TLC: $R_f$=0.63 (10% MeOH/DCM).

Referring to Scheme 3, synthesis of compound 20, a three-necked round-bottomed flask equipped with a thermometer was charged with compound 19 (1.2 g, 5.1 mmol), toluene (8 mL), THF (3 mL), and triisopropylborate (1.4 mL, 6.0 mmol). After cooling to −40° C. (dry ice/acetone), n-butyllithium (1.6 M in hexanes, 3.75 mL) was slowly added over the course of 30 min. The reaction was then allowed to warm to −20° C., and HCl (2M, 5 mL) was added. When the reaction reached room temperature, the aqueous layer was removed and adjusted to pH 7.6 with NaOH (3M, 2 mL), saturated with NaCl, and extracted with THF (3×6 mL). The THF layers were combined, dried with $MgSO_4$, evaporated to an oil, diluted with $CH_3CN$ (40 mL), and heated at 70° C. for 30 min. The solution was let crystallize at 4° C. for 72 h. The yellow solid was filtered, washed with ice-cold $CH_3CN$, and air-dried (0.38 g, 37%).

Referring to Scheme 3, synthesis of compound 21, to a suspension of methyl 3,5-dibromobenzoate (0.55 g, 1.88 mmol) and compound 20 (0.94 g, 4.7 mmol) in anhydrous 1,4-dioxane (20 mL), was added an aqueous solution of $K_3PO_4$ (2 M, 3 mL), followed by $PPh_3$ (0.21 g, 0.8 mmol) and $Pd(OAc)_2$ (0.05 g, 0.2 mmol). The reaction was refluxed for 20 h. while a gentle and steady stream of argon was bubbled through the solution. After cooling to room temperature, EtOAc (30 mL) was added and the biphasic reaction was filtered. The organic layer was separated, washed with water (20 mL) and brine (20 mL), dried over $MgSO_4$, concentrated in vacuo, and purified by flash column chromatography (2%-20% methanol in $CHCl_3$) to give compound 21 (0.28 g, 35%). TLC: $R_f$=0.43 (10% MeOH/$CHCl_3$).

Referring to Scheme 3, synthesis of compound 22, to a suspension of compound 21 (0.29 g, 0.65 mmol) in methanol (6 mL), THF (6 mL), and water (3 mL), was added LiOH (0.05 g, 2 mmol), and the reaction was stirred for 30 min. at room temperature, then increased to 50° C. for 10 min. (reaction became clear). After stirring at room temperature for an addition 2 h., the volatile solvents were evaporated in vacuo. More water (20 mL) was added, and the pH was adjusted to pH 5 with $KHSO_4$ (1 M), resulting in precipitate formation. The precipitate was collected by filtration, washed with water, and dried under vacuum to yield 22 (0.26 g, 93%).

Referring to Scheme 3, synthesis of compound 23, to a cooled (0° C.) suspension of compound 22 (0.26 g, 0.6 mmol) in dichloromethane (30 mL), was added N-(3-dimethylaminopropyl)-N'-ethylcarbodiimide hydrochloride (0.14 g, 0.72 mmol), 1-hydroxy-benzotriazole hydrate (0.1 g, 0.72 mmol), and triethylamine (0.1 mL, 0.72 mmol). After stirring for 30 min. at 0° C., N-(3-aminopropyl)methacrylamide hydrochloride (0.13 g, 0.72 mmol) and triethylamine (0.2 mL, 1.44 mmol) were added. The reaction was stirred for 24 h. After the addition of saturated $NaHCO_3$ (20 mL), a significant amount of solid remained in both layers. The solid was filtered and saved. The aqueous layer was extracted with DCM (3×30 mL). The solid that was filtered in the previous step was combined with the DCM extractions and purified by flash column chromatography (5%-20% methanol in DCM) to give compound 23 (0.23 g, 70%) as a white solid. TLC: $R_f$=0.21 (10% MeOH/DCM).

Referring to Scheme 3, synthesis of B-C, 2-Bromomethylphenyl boronic acid (0.53 g, 2.5 mmol) was added to a solution of compound 23 (0.23 g, 0.41 mmol) in DMF (3 mL) and ethylene glycol (0.14 mL, 2.5 mmol). The reaction was stirred at 55° C. for 72 h. Diethylether (30 mL) was added to separate the product as an oil. The solvent was decanted, and the remaining oil was sonicated in acetone until it became a pale yellow powder. The solid was collected by centrifugation, washed with acetone several times and dried under argon (0.47 g, 81%).

Example 4

SYNTHESIS OF Q-4 (SCHEME 4)

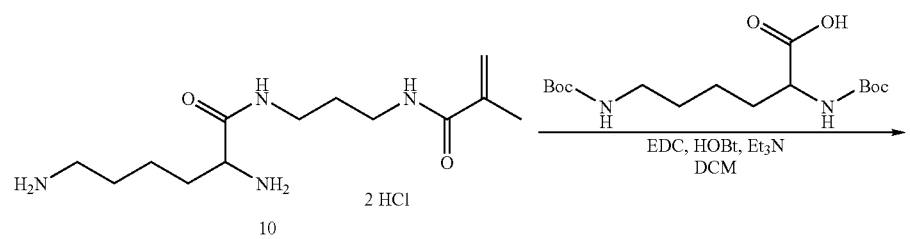

10

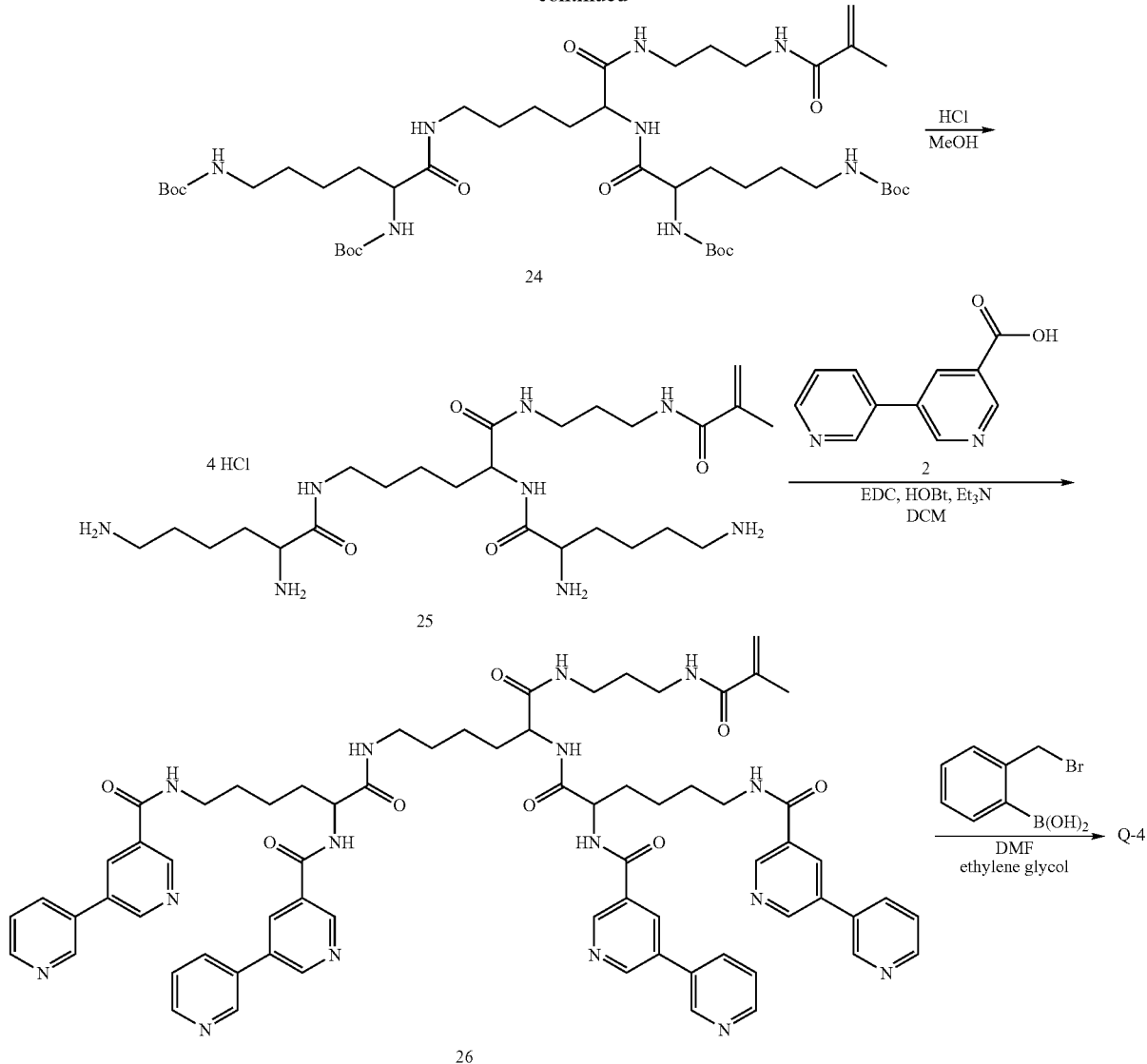

Referring to Scheme 4 (synthesis of Q-4), synthesis of compound 25, to a cooled (0° C.) solution of N,N-di-boc-lysine (dicyclohexylammonium) salt (4.4 g, 8.3 mmol) in dichloromethane (200 mL), was added N-(3-dimethylamino-propyl)-N'-ethylcarbodiimide hydrochloride (1.7 g, 8.8 mmol), 1-hydroxy-benzotriazole hydrate (1.2 g, 8.8 mmol), and triethylamine (1.2 mL, 8.8 mmol). After stirring for 30 min. at 0° C., compound 10 (1.29 g, 3.76 mmol) and triethylamine (1.0 mL, 7.6 mmol) were added. The reaction was stirred for 24 h., then washed with saturated NaHCO$_3$ (3×100 mL). The DCM layer was dried with MgSO$_4$, reduced in volume in vacuo, and purified by flash column chromatography (2%-20% methanol in CHCl$_3$) to give compound 24. TLC: R$_f$=0.56 (10% MeOH/DCM). The appropriate fractions were pooled and concentrated to about 5 mL, then diluted with methanolic HCl (0.5 M, 100 mL) and ethereal HCl (2 M, 10 mL), and stirred for 16 h. The reaction was concentrated in vacuo to an oil, washed with acetone, and dried under vacuum to give 25 as a white foam (2.25 g, 89%).

Referring to Scheme 4, synthesis of compound 26, to a cooled (0° C.) suspension of compound 2 (3.0 g, 15 mmol) in dichloromethane (250 mL), was added N-(3-dimethylamino-propyl)-N'-ethylcarbodiimide hydrochloride (3.45 g, 18 mmol), 1-hydroxy-benzotriazole hydrate (2.43 g, 18 mmol), and triethylamine (2.5 mL, 18 mmol). After stirring for 30 min. at 0° C., compound 25 (2.25 g, 3.3 mmol) and triethylamine (1.8 mL, 13 mmol) were added. The reaction was stirred for 18 h. White precipitate formed. After the addition of saturated NaHCO$_3$ (100 mL), a significant amount of solid remained in both layers. The solid was filtered, washed with acetone, then sonicated in water (150 mL). The gooey solid that remained insoluble in water was collected, dissolved in methanol (50 mL), filtered to remove salt, and evaporated in vacuo to give 26 as a pale yellow solid (1.25 g, 30%).

Referring to Scheme 4, synthesis of Q-4,2-Bromomethylphenyl boronic acid (0.6 g, 2.8 mmol) was added to a solution of compound 26 (0.3 g, 0.24 mmol) in DMF (4 mL) and ethylene glycol (0.2 mL, 3.5 mmol). The reaction was stirred at 60° C. for 72 h. Acetone (20 mL) was added to precipitate the product as yellow solid, which was collected by centrifugation, washed with acetone several times and dried under argon (0.65 g, 91%).

Example 5

HPTS-TriCys-MA Dye and Quenchers B-1, B-2, B-3 and B-4 Immobilized within a Hydrogel at the End of a Fiber Optic Sensor The appropriate amount of a quencher was dissolved in 414 µL of a stock solution containing N,N'-dimethylacrylamide (500 mg) and N,N'-methylenebismethacrylamide (10 mg) to give a quencher stock solution (9.66 mM). This quencher solution (20.7 µL) was then added to a solution containing HPTS-TriCys-MA (50 µL of a 2 mM aqueous solution), HCl (20 µL of a 100 mM solution), 2,2'-azobis[2-(2-imidazolin-2-yl)propane]dihydrochloride (10 µL, of a 40 mg/mL solution), and DI water (99.3 µL). Some of this solution was then polymerized onto the tip of a fiber optic sensor by heating at 37° C. for 24 h. to form a hydrogel.

FIG. 1 illustrates the glucose response of the above-described sensors comprising one of quenchers B-1, B-2, B-3 and B-4, and dye HPTS-triCys-MA, immobilized within a hydrogel at the tip of an optical fiber. The detection chemistry was excited at 470 nm and fluorescence was measured between 520-700 nm in the presence of increasing concentrations of glucose.

Example 6

HPTS-TriCys-MA Dye and Quenchers B-4, B-C and Q-4 Immobilized within a Hydrogel at the End of a Fiber Optic Sensor The appropriate amount of a quencher was dissolved in 200 µL of a stock solution containing N,N'-dimethylacrylamide (100 mg) and N,N'-methylenebismethacrylamide (2 mg) to give a quencher stock solution (B-4 and B-C=19.32 mM, Q-4=9.66 mM). This quencher solution (20.7 µL) was then added to a solution containing HPTS-TriCys-MA (50 µL of a 2 mM aqueous solution), HCl (20 µL of a 100 mM solution), 2,2'-azobis[2-(2-imidazolin-2-yl)propane]dihydrochloride (40 µL, of a 50 mg/mL solution), and DI water (69.3 µL). Some of this solution was then polymerized onto the tip of a fiber optic sensor by heating at 37° C. for 16 h. to form a hydrogel.

Figure 2:
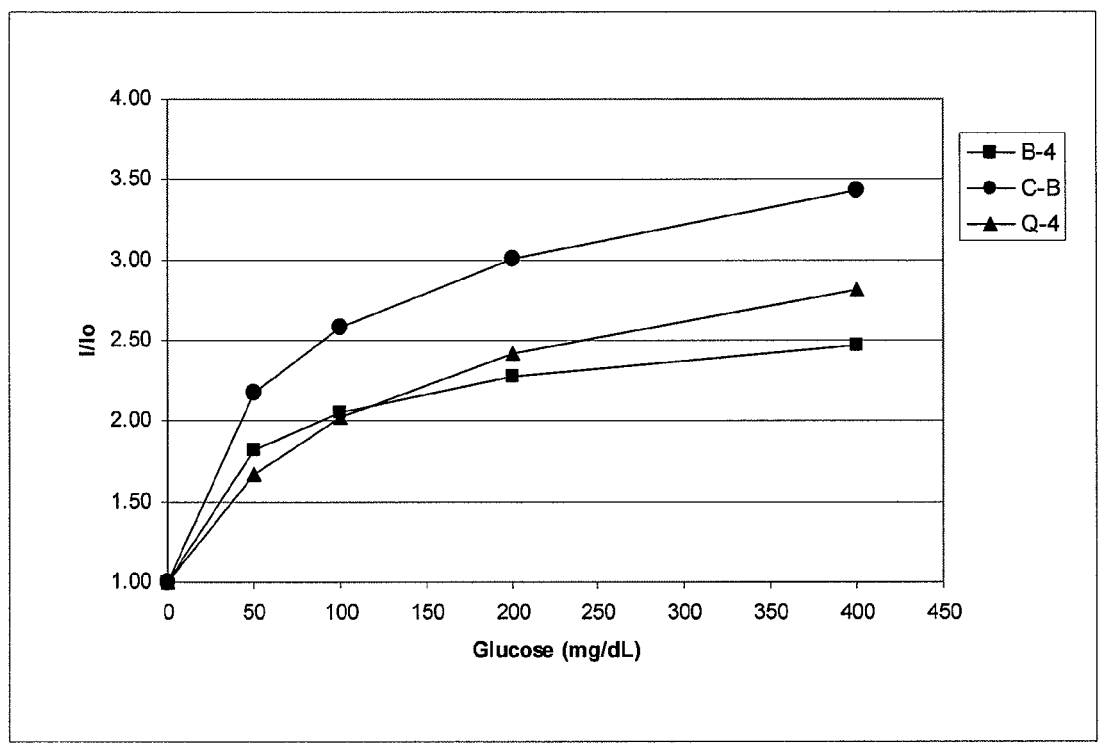
FIG. 2 illustrates the glucose response of the above-described sensors comprising one of quenchers B-4, B-C and Q-4, and dye HPTS-triCys-MA, immobilized within a hydrogel at the tip of an optical fiber. The detection chemistry was excited at 470 nm and fluorescence was measured between 520-700 nm in the presence of increasing concentrations of glucose.

FIG. 2 illustrates the glucose response of the above-described sensors comprising one of quenchers B-4, B-C and Q-4, and dye HPTS-triCys-MA, immobilized within a hydrogel at the tip of an optical fiber. The detection chemistry was excited at 470 nm and fluorescence was measured between 520-700 nm in the presence of increasing concentrations of glucose.

While the present invention has been described in some detail for purposes of clarity and understanding, one skilled in the art will appreciate that various changes in form and detail can be made without departing from the true scope of the invention. All figures, tables, and appendices, as well as patents, applications, and publications, referred to above, are hereby incorporated by reference.

What is claimed is:

1. A polyviologen compound comprising two or more viologen moieties, wherein each viologen moiety includes at least two boronic acid functional groups, and wherein the polyviologen compound comprises a coupling group.

2. The polyviologen compound of claim 1, wherein the polyviologen is derived from a 3,3' dipyridyl intermediate.

3. A compound of claim 1 having the following structure:

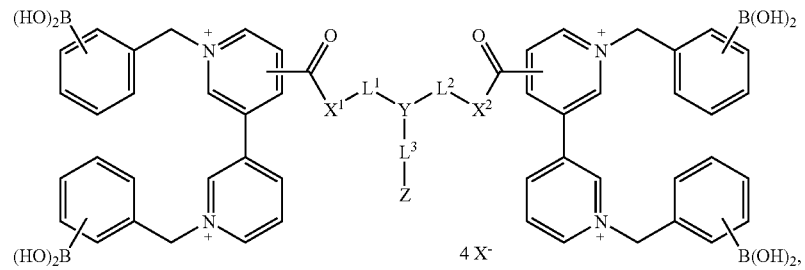

wherein

Z is either a reactive, ethylenically unsaturated group or a reactive functional group, capable of forming a covalent bond with a polymer or matrix;

Y is a trivalent connecting group selected from

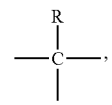

where R is H or a lower alkyl, and

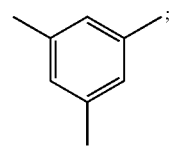

$X^-$ is a counterion;

$X^1$ and $X^2$ are —O— or —NH—; and $L^1$, $L^2$, and $L^3$ are selected from the group consisting of a direct bond and a lower alkylene having 1 to 8 carbon atoms, optionally terminated with or interrupted by one or more divalent connecting groups selected from the group consisting of sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH— and amine —NR— (where R is defined as alkyl having 1 to 6 carbon atoms) or combinations thereof.

4. The compound of claim 3 wherein Z is a reactive, ethylenically unsaturated group selected from the group consisting of methacrylamido-, acrylamido-, methacryloyl-, acryloyl- and styryl-.

5. The compound of claim 3 wherein Z is a reactive functional group, capable of forming a covalent bond with a polymer or matrix selected from the group consisting of —Br, —OH, —SH, —CO$_2$H, and —NH$_2$.

6. The compound of claim 3 wherein Z is

wherein R is H or CH$_3$.

7. A compound of claim 1 having the following structure:

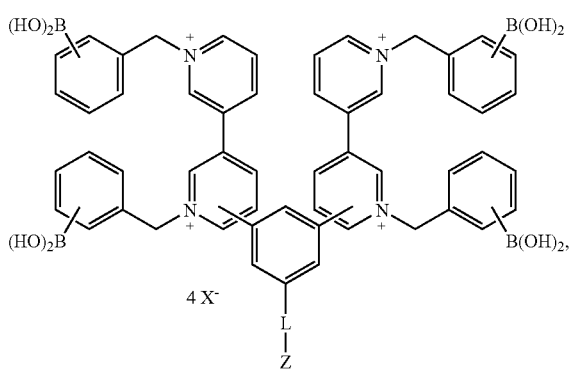

wherein
X$^-$ is a counterion;
L is a divalent linking selected from the group consisting of a direct bond and a lower alkylene having 1 to 8 carbon atoms, optionally terminated with or interrupted by one or more divalent connecting groups selected from the group consisting of sulfonamide (—SO$_2$NH—), amide —(C=O)N—, ester —(C=O)—O—, ether —O—, sulfide —S—, sulfone (—SO$_2$—), phenylene —C$_6$H$_4$—, urethane —NH(C=O)—O—, urea —NH(C=O)NH—, thiourea —NH(C=S)—NH—, amide —(C=O)NH— and amine —NR— (where R is defined as alkyl having 1 to 6 carbon atoms) or combinations thereof;
Z is either a reactive, ethylenically unsaturated group or a reactive functional group, capable of forming a covalent bond with a polymer or matrix;
the bond from the central benzene ring is to the ortho, meta or para position on the adjacent pyridinium rings; and
—B(OH)$_2$ may be in the ortho, meta or para position.

8. The compound of claim 7 wherein Z is a reactive, ethylenically unsaturated group selected from the group consisting of methacrylamido-, acrylamido-, methacryloyl-, acryloyl- and styryl-.

9. The compound of claim 7 wherein Z is a reactive functional group, capable of forming a covalent bond with a polymer or matrix selected from the group consisting of —Br, —OH, —SH, —CO$_2$H, and —NH$_2$.

10. The compound of claim 7 wherein Z is

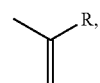

wherein R is H or CH$_3$.

11. A compound of claim 7 having the following structure:

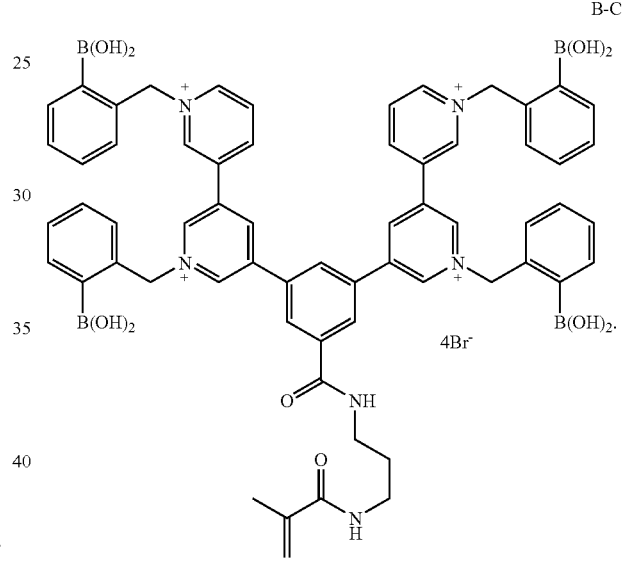

12. A method of making the compound of claim 11, comprising the steps of:

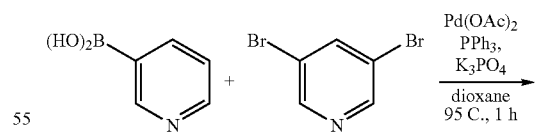

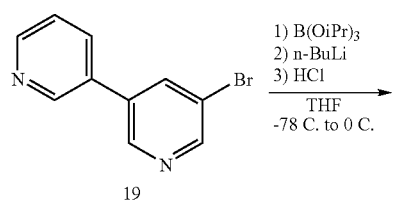

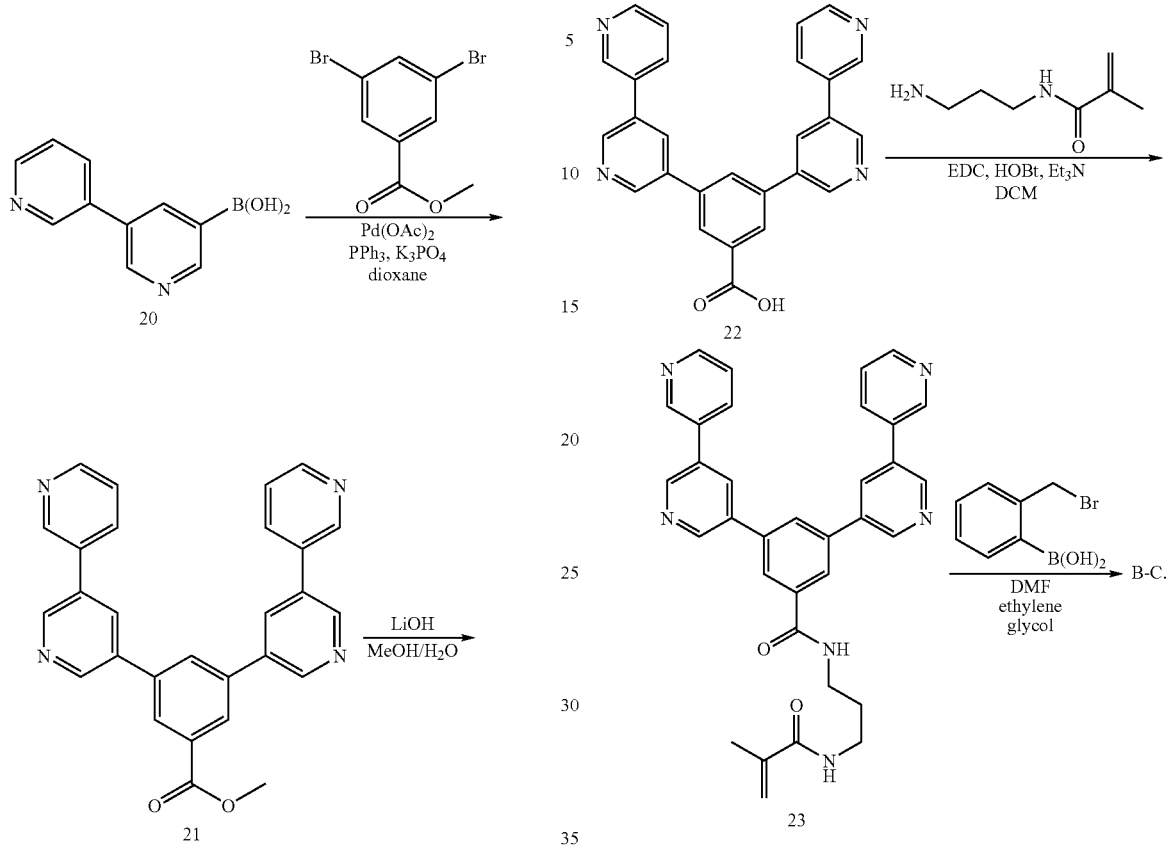
13. A compound of claim 1 having the following structure:
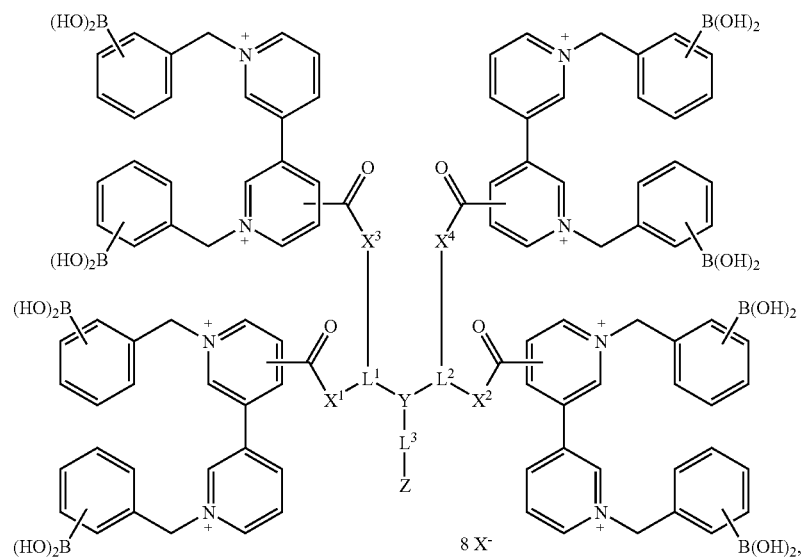

wherein:
  Z is either a reactive, ethylenically unsaturated group or a reactive functional group, capable of forming a covalent bond with a polymer or matrix;
  Y is a trivalent connecting group selected from

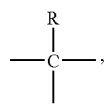

where R is H or a lower alkyl, and

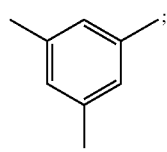

X⁻ is a counterion;
X¹, X², X³ and X⁴ are —O— or —NH—; and
L¹, L², and L³ are selected from the group consisting of a direct bond and a lower alkylene having 1 to 8 carbon atoms, optionally terminated with or interrupted by one or more divalent connecting groups selected from the group consisting of sulfonamide (—SO₂NH—), amide —(C=O)N—, ester —(C=O)—O—, ether —O—, sulfide —S—, sulfone (—SO₂—), phenylene —C₆H₄—, urethane —NH(C=O)—O—, urea —NH(C=O)NH—, thiourea —NH(C=S)—NH—, amide —(C=O)NH— and amine —NR— (where R is defined as alkyl having 1 to 6 carbon atoms) or combinations thereof.

14. The compound of claim 13 wherein Z is a reactive, ethylenically unsaturated group selected from the group consisting of methacrylamido-, acrylamido-, methacryloyl-, acryloyl- and styryl-.

15. The compound of claim 13 wherein Z is a reactive functional group, capable of forming a covalent bond with a polymer or matrix selected from the group consisting of —Br, —OH, —SH, —CO₂H, and —NH₂.

16. The compound of claim 13 wherein Z is

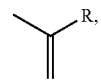

wherein R is H or CH₃.

17. A compound of claim 13 having the following structure:

Q-4

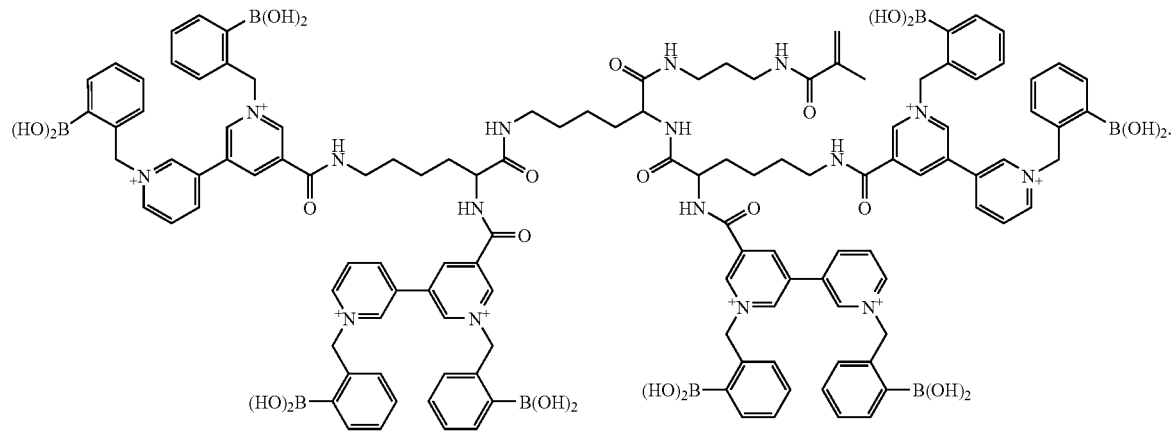

18. A method of making the compound of claim 17, comprising the steps of:
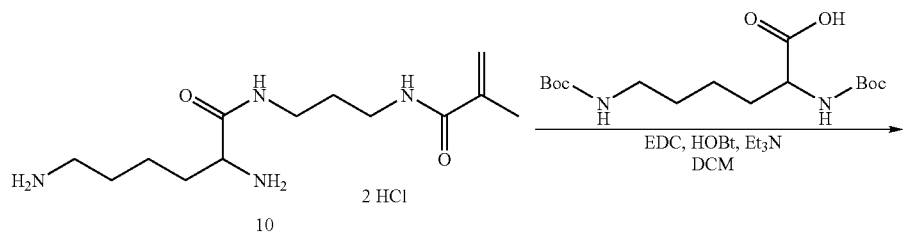
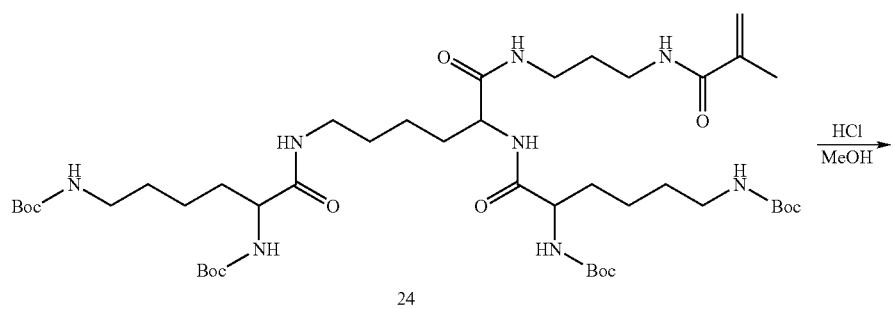
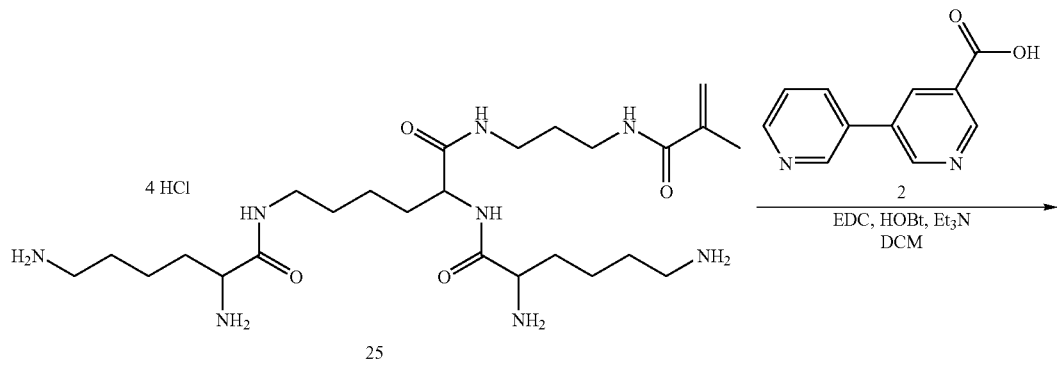
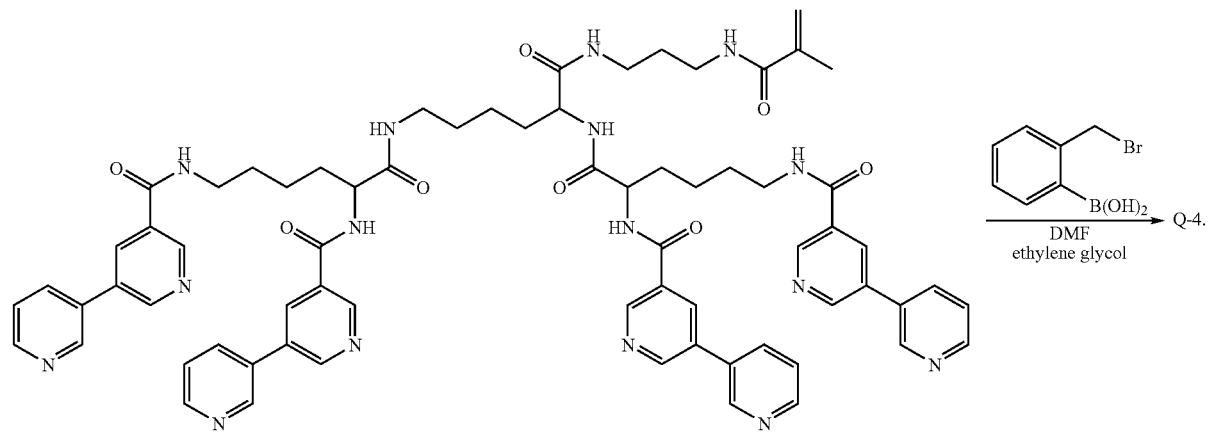

19. The compound:
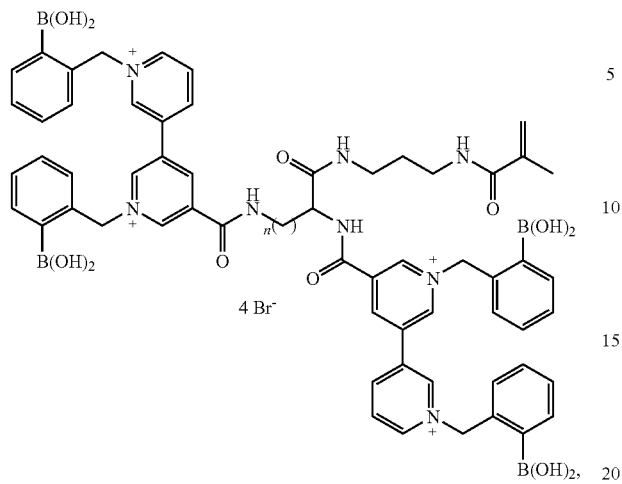
wherein n is equal to 1, 2, 3, or 4.
20. A method of making the compound of claim 19, comprising the steps of:
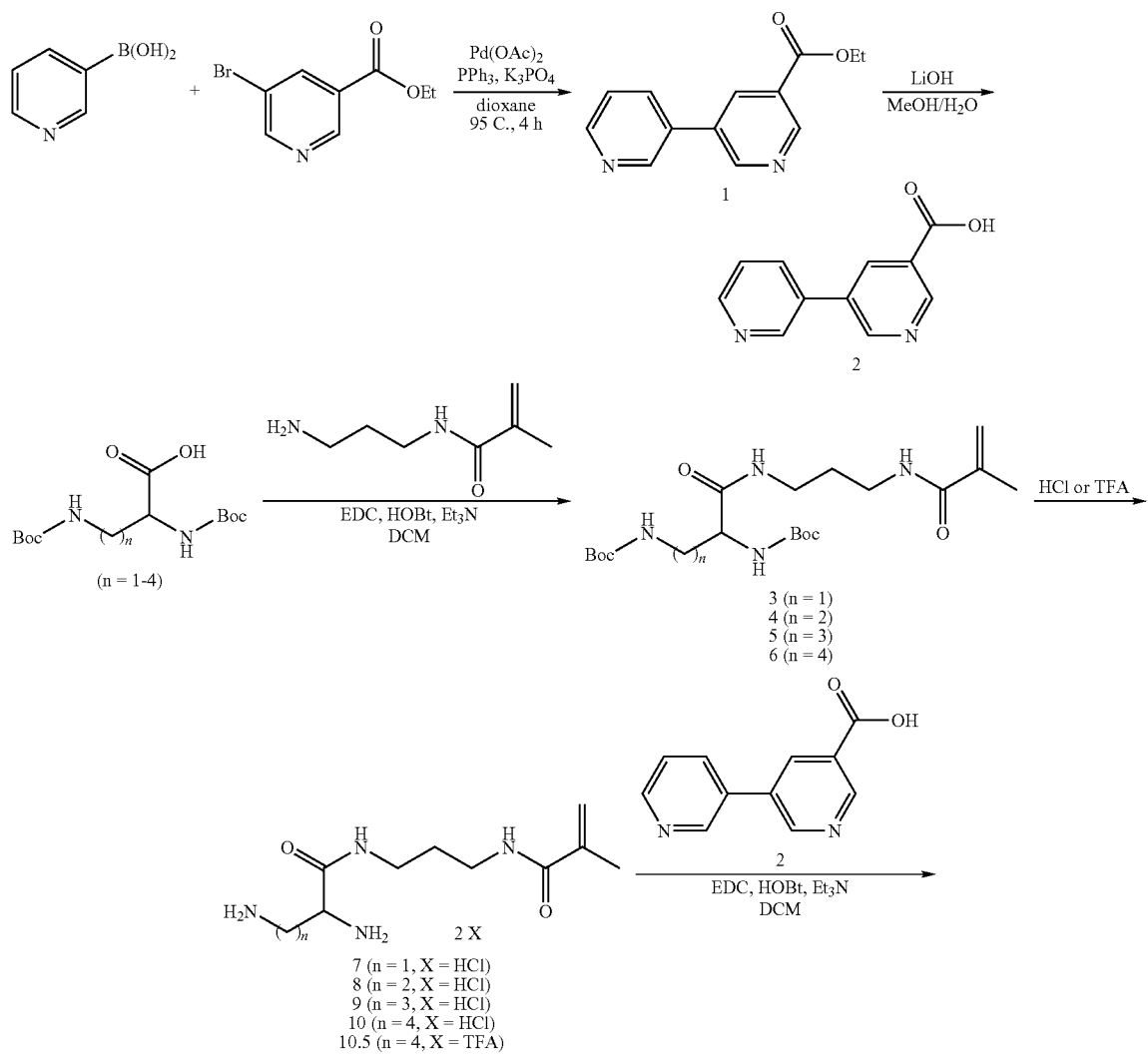

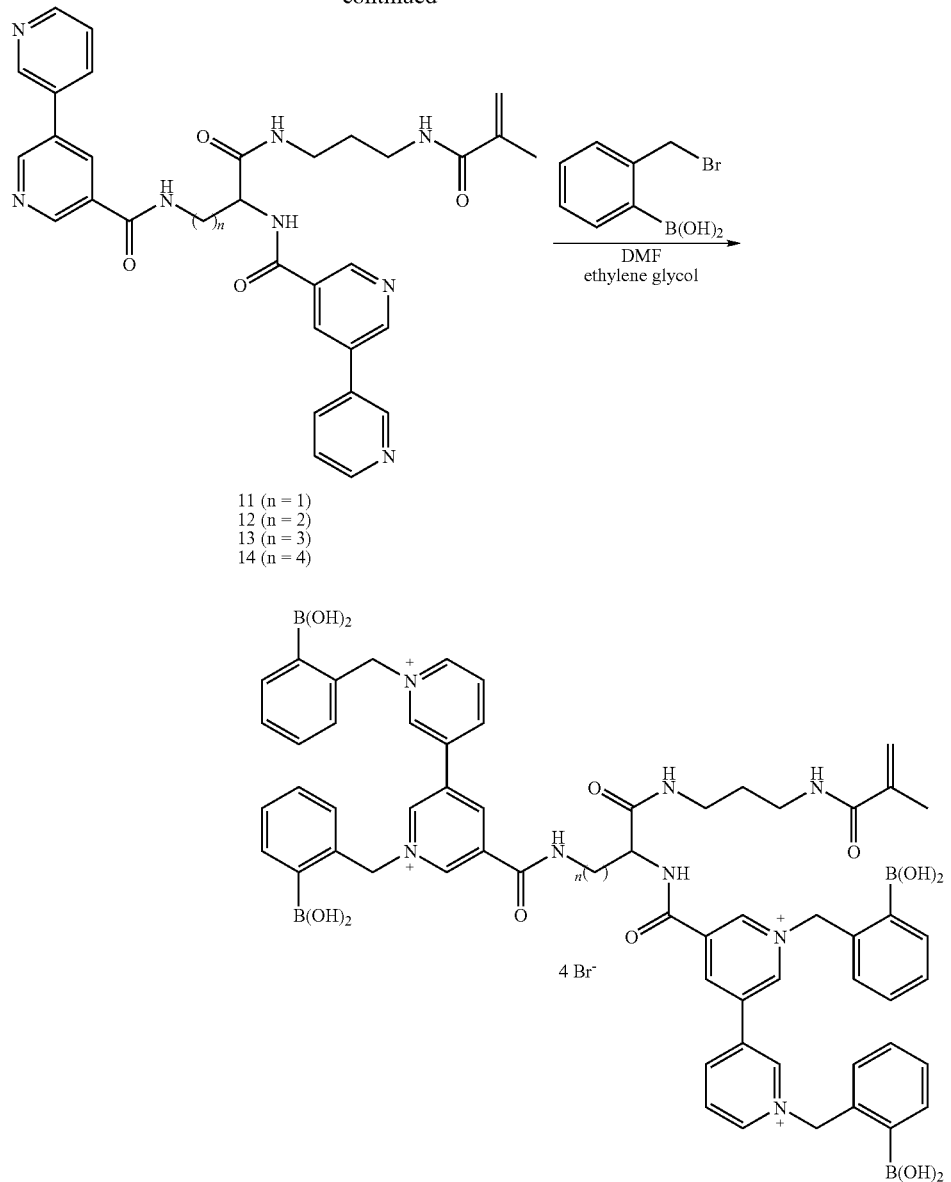
wherein n is equal to 1, 2, 3, or 4.
21. A method of making the compound of claim 19 comprising the steps of:
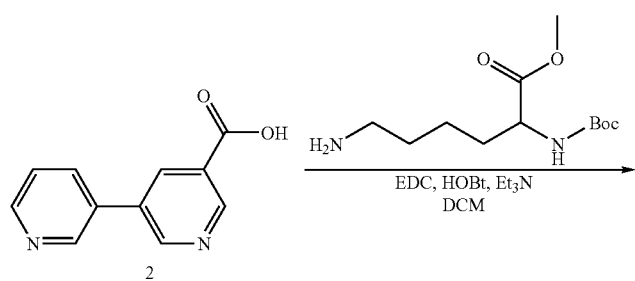

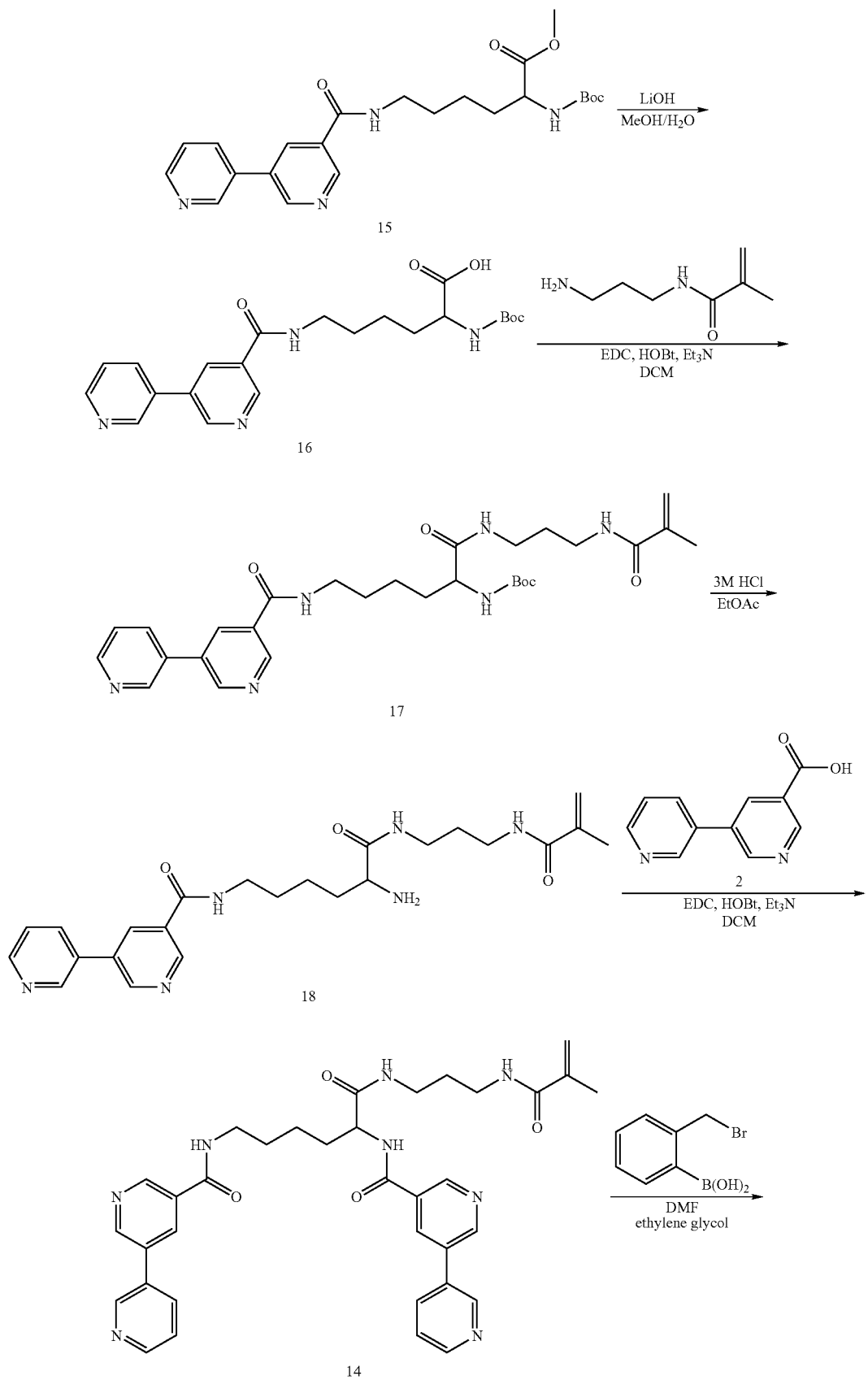

-continued

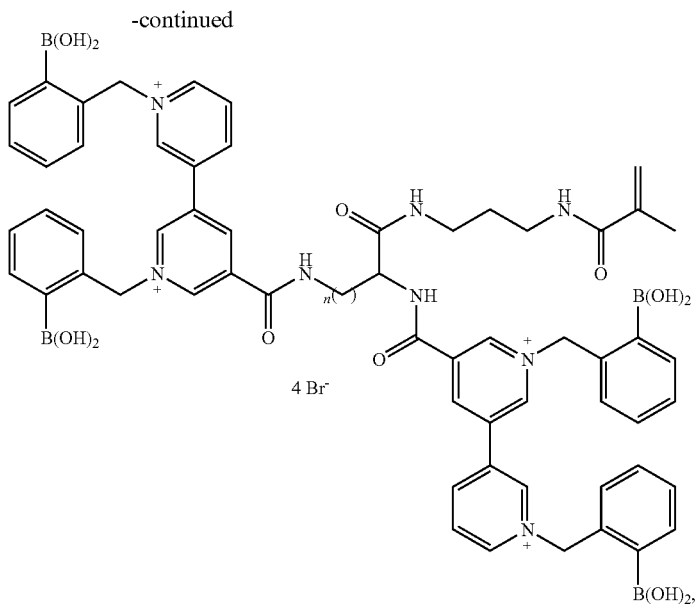

wherein n is equal to 4.

22. An analyte sensor, comprising any one or more of the compounds of claims 1-19, 7-11 and 13-17 and a fluorescent dye.

23. The analyte sensor of claim 22, wherein said any one or more of the compounds are in the form of a polymer.

24. The analyte sensor of claim 22, wherein the analyte is glucose.

25. The analyte sensor of claim 24, further comprising a glucose permeable immobilizing means.

26. The analyte sensor of claim 24, wherein said glucose permeable immobilizing means is a polymer matrix or a semipermeable membrane.

27. A composition of matter, comprising a fluorophore that is susceptible to quenching by a viologen, a polyviologen derived from a 3,3' dipyridyl intermediate comprising two or more viologen moieties, wherein each viologen moiety includes at least two boronic acid functional groups, and a glucose permeable polymer matrix.

28. The composition of claim 27, wherein the fluorophore has at least one negative charge.

* * * * *